(12) United States Patent
Sparks et al.

(10) Patent No.: US 10,478,421 B1
(45) Date of Patent: Nov. 19, 2019

(54) SORTILIN BINDING COMPOUNDS, FORMULATIONS, AND USES THEREOF

(71) Applicants: Robert Pleasants Sparks, Urbana, IL (US); Wayne Charles Guida, St. Pete Beach, FL (US); Janet Lindsay DeHoff-Sparks, Pittsford, NY (US)

(72) Inventors: Robert Pleasants Sparks, Urbana, IL (US); Wayne Charles Guida, St. Pete Beach, FL (US); Janet Lindsay DeHoff-Sparks, Pittsford, NY (US)

(73) Assignees: University of Florida, Tampa, FL (US); University of Rochester, Rochester, NY (US)

( * ) Notice: Subject to any disclaimer, the term of this patent is extended or adjusted under 35 U.S.C. 154(b) by 0 days.

(21) Appl. No.: 16/148,839

(22) Filed: Oct. 1, 2018

Related U.S. Application Data

(63) Continuation of application No. 15/431,568, filed on Feb. 13, 2017, now Pat. No. 10,085,969.

(60) Provisional application No. 62/294,412, filed on Feb. 12, 2016.

(51) Int. Cl.
*A61K 31/40* (2006.01)
*A61K 31/167* (2006.01)
*C07D 207/09* (2006.01)
*C07D 333/46* (2006.01)
*A61K 31/381* (2006.01)

(52) U.S. Cl.
CPC ............ *A61K 31/40* (2013.01); *A61K 31/167* (2013.01); *A61K 31/381* (2013.01); *C07D 207/09* (2013.01); *C07D 333/46* (2013.01)

(58) Field of Classification Search
CPC .............................. A61K 31/40; A61K 31/167
USPC ......................... 514/408, 629, 630
See application file for complete search history.

(56) References Cited

U.S. PATENT DOCUMENTS 8,703,947 B2 * 4/2014 Ghosh .................. C07D 207/08
544/367

* cited by examiner

*Primary Examiner* — Matthew P Coughlin
*Assistant Examiner* — Sagar Patel
(74) *Attorney, Agent, or Firm* — Thomas|Horstemeyer, LLP

(57) ABSTRACT

Provided herein are compounds and formulations thereof that can be capable of binding to sortilin or an analogue thereof. Also provided herein are methods of administering the compounds and formulation provided herein to a subject in need thereof.

12 Claims, 14 Drawing Sheets

Cpd984 High Range

Cpd984 High Range

Cpd984 Low Range

SORTILIN BINDING COMPOUNDS, FORMULATIONS, AND USES THEREOF

CROSS-REFERENCE TO RELATED APPLICATIONS

This application is a continuation of co-pending U.S. patent application Ser. No. 15/431,568, filed on Feb. 13, 2017, entitled "SORTILIN BINDING COMPOUNDS, FORMULATIONS, AND USES THEREOF," the contents of which is incorporated by reference herein in its entirety.

U.S. patent application Ser. No. 15/431,568 claims the benefit of and priority to U.S. Provisional Patent Application No. 62/294,412, filed on Feb. 12, 2016, entitled "LOWERING LDL CHOLESTEROL AND ASSOCIATED CARDIOVASCULAR DISEASE RISK BY INCREASING HEPATIC LDL RECEPTORS BY BLOCKING SECRETION OF PCSK9 THROUGH INTERFERENCE BY SMALL MOLECULES WITH PCSK9 INTERACTION WITH SORTILIN," the contents of which is incorporated by reference herein in its entirety.

STATEMENT REGARDING FEDERALLY SPONSORED RESEARCH OR DEVELOPMENT

This invention was made with government support under grants number DK100163-01A1 and GM101132 awarded by the National Institutes of Health. The government has certain rights in the invention.

SEQUENCE LISTING

This application contains a sequence listing filed in electronic form as an ASCII.txt file entitled 292105-1110_ST25.txt, created on Feb. 13, 2017. The content of the sequence listing is incorporated herein in its entirety.

BACKGROUND

Proprotein convertase subtillisin/kexin type 9 (PCSK9) is an enzyme that is ubiquitously expressed in many tissues and binds to the receptor of low-density lipoprotein (LDL) particles. The LDL receptor (LDLR) binds and transports LDL-particles into cells and thus can reduce the concentration of LDL in circulation. While the LDLR has be the focus of much research and the target of many therapeutics aimed at treating high cholesterol, there still exists a need for improved and alternative treatments.

SUMMARY

Provided herein are compounds that can have a structure according to Formula 2

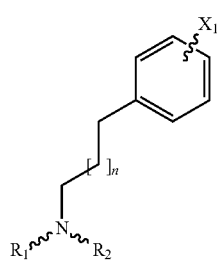

Formula 2 where n can be 1-10, where $X_1$ can be selected from the group of: H, a $C_1$-$C_5$ unsubstituted or substituted alkyl, a $C_1$-$C_5$ cyclic alkyl where at least 2 carbon atoms of the $C_1$-$C_5$ cyclic alkyl are members of the benzene ring of Formula 2, an acyl, an amino a sulfono, a chloro, a bromo, a iodo, a flouro, and permissible combinations thereof, where $R_1$ can be a carboxcylic acid or an ester where $R_2$ can be a 5, 6, or 7 member heterocyclic ring that can be optionally further substituted with a suitable substituent, a sulfonium, a quaternary ammonium,

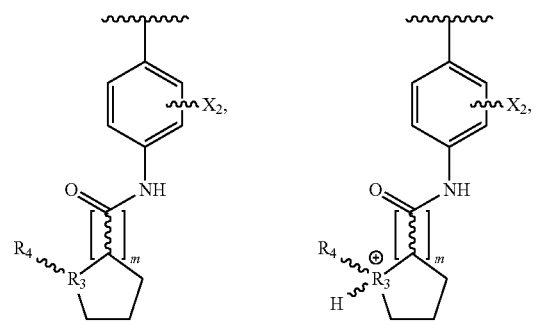

where $X_2$ can be selected from the group of: H, a $C_1$-$C_5$ unsubstituted or substituted alkyl, a $C_1$-$C_5$ cyclic alkyl where at least 2 carbon atoms of the $C_1$-$C_5$ cyclic alkyl are members of the benzene ring of Formula 2, an acyl, an amino a sulfono, a chloro, a bromo, a iodo, a flouro, and permissible combinations thereof, where $R_3$ can be N or S, where $R_4$ can be H, an $C_1$-$C_{10}$ alkyl, an amino, a carboxylic acid, an ester, an amino acid or positively charged derivative thereof, and where m represents the number of carbon atoms in an alkyl and can range from 0-10. The compound(s) can bind Site 2 on sortilin or analogue thereof. In some embodiments, the compound can bind to Site 2 on sortilin or analogue thereof and can increase binding of a compound to site 1 of sortilin or an analogue thereof. In some embodiments the compound can have a structure according to Formula 2A

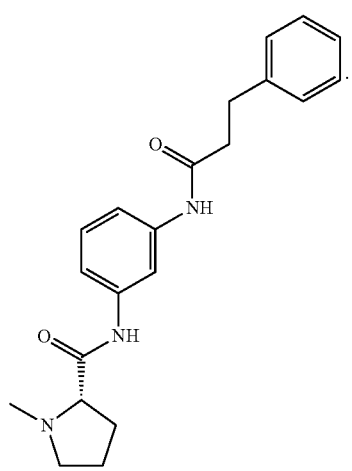

Formula 2A

In some embodiments the compound can have a structure according to Formula 2B

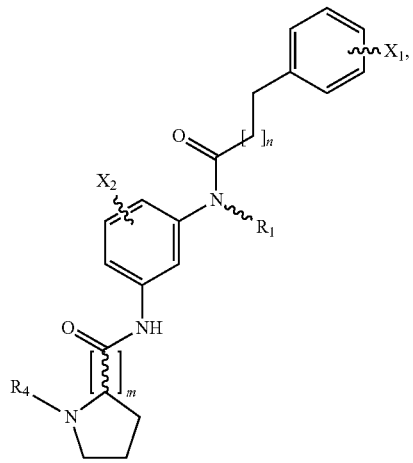

Formula 2B where $X_1$ and $X_2$ can each be independently selected from the group of: H, a $C_1$-$C_5$ unsubstituted or substituted alkyl, a $C_1$-$C_5$ cyclic alkyl where at least 2 carbon atoms of the $C_1$-$C_5$ cyclic alkyl are members of the benzene ring of Formula 2B, an acyl, an amino a sulfono, a chloro, a bromo, a iodo, a flouro, and permissible combinations thereof, where Ft, can be a carboxcylic acid or an ester, where $R_4$ can be H, an $C_1$-$C_{10}$ alkyl, an amino, a carboxylic acid, an ester, an amino acid or positively charged derivative thereof, where n can be 1-10, and where m represents the number of carbon atoms in an alkyl, where m can range from 0-10.

Also provided herein are pharmaceutical formulations that can include a compound having a structure according to Formula 2,

Formula 2 where n can be 1-10, where $X_1$ can be selected from the group of: H, a $C_1$-$C_5$ unsubstituted or substituted alkyl, a $C_1$-$C_5$ cyclic alkyl where at least 2 carbon atoms of the $C_1$-$C_5$ cyclic alkyl are members of the benzene ring of Formula 2, an acyl, an amino a sulfono, a chloro, a bromo, a iodo, a flouro, and permissible combinations thereof, where $R_1$ can be a carboxcylic acid or an ester where $R_2$ can be a 5, 6, or 7 member heterocyclic ring that can be optionally further substituted with a suitable substituent, a sulfonium, a quaternary ammonium,

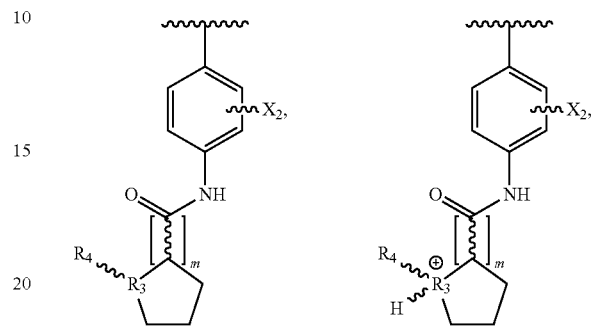

where $X_2$ can be selected from the group of: H, a $C_1$-$C_5$ unsubstituted or substituted alkyl, a $C_1$-$C_5$ cyclic alkyl where at least 2 carbon atoms of the lea-$C_5$ cyclic alkyl are members of the benzene ring of Formula 2, an acyl, an amino a sulfono, a chloro, a bromo, a iodo, a flouro, and permissible combinations thereof, where $R_3$ can be N or S, where $R_4$ can be H, an $C_1$-$C_{10}$ alkyl, an amino, a carboxylic acid, an ester, an amino acid or positively charged derivative thereof, and where m represents the number of carbon atoms in an alkyl and can range from 0-10; and a pharmaceutically acceptable carrier. The compound(s) can bind Site 2 on sortilin or analogue thereof. In some embodiments, the compound can bind to Site 2 on sortilin or analogue thereof and can increase binding of a compound to site 1 of sortilin or an analogue thereof. In some embodiments the compound can have a structure according to Formula 2A

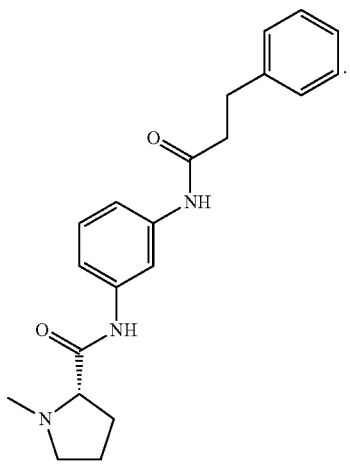

Formula 2A

In some embodiments the compound can have a structure according to Formula 2B

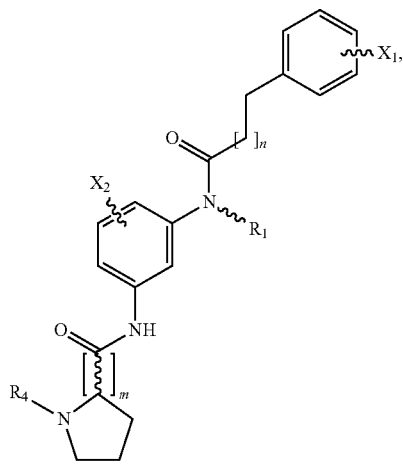

Formula 2B where $X_1$ and $X_2$ can each be independently selected from the group consisting of: H, a $C_1$-$C_5$ unsubstituted or substituted alkyl, a $C_1$-$C_5$ cyclic alkyl where at least 2 carbon atoms of the $C_1$-$C_5$ cyclic alkyl are members of the benzene ring of Formula 2B, an acyl, an amino a sulfono, a chloro, a bromo, a iodo, a flouro, and permissible combinations thereof, where $R_1$ can be a carboxcylic acid or an ester, where $R_4$ can be H, an $C_1$-$C_{10}$ alkyl, an amino, a carboxylic acid, an ester, an amino acid or positively charged derivative thereof, where n can be 1-10, and where m represents the number of carbon atoms in an alkyl, where m can range from 0-10.

Also provided herein are methods that can include the step of contacting sortilin or an analogue thereof with an amount of a compound having a structure according to Formula 2

Formula 2 where n can be 1-10, where $X_1$ can be selected from the group of: H, a $C_1$-$C_5$ unsubstituted or substituted alkyl, a $C_1$-$C_5$ cyclic alkyl where at least 2 carbon atoms of the $C_1$-$C_5$ cyclic alkyl are members of the benzene ring of Formula 2, an acyl, an amino a sulfono, a chloro, a bromo, a iodo, a flouro, and permissible combinations thereof, where $R_1$ can be a carboxcylic acid or an ester where $R_2$ can be a 5, 6, or 7 member heterocyclic ring that can be optionally further substituted with a suitable substituent, a sulfonium, a quaternary ammonium,

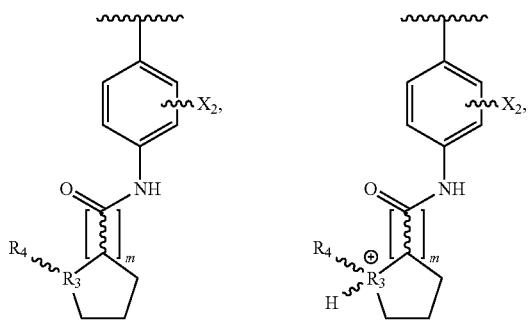

where $X_2$ can be selected from the group of: H, a $C_1$-$C_5$ unsubstituted or substituted alkyl, a $C_1$-$C_5$ cyclic alkyl where at least 2 carbon atoms of the $C_1$-$C_5$ cyclic alkyl are members of the benzene ring of Formula 2, an acyl, an amino a sulfono, a chloro, a bromo, a iodo, a flouro, and permissible combinations thereof, where $R_3$ can be N or S, where $R_4$ can be H, an $C_1$-$C_{10}$ alkyl, an amino, a carboxylic acid, an ester, an amino acid or positively charged derivative thereof, and where m represents the number of carbon atoms in an alkyl and can range from 0-10. The compound(s) can bind Site 2 on sortilin or analogue thereof. In some embodiments, the compound can bind to Site 2 on sortilin or analogue thereof and can increase binding of a compound to site 1 of sortilin or an analogue thereof. In some embodiments the compound can have a structure according to Formula 2A

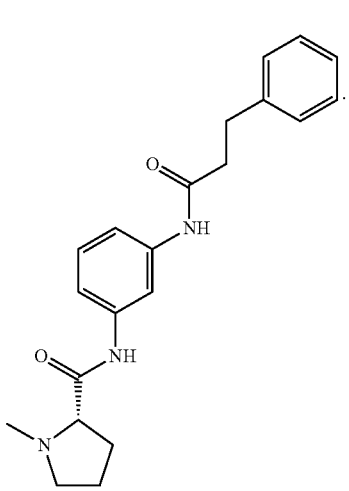

Formula 2A

In some embodiments the compound can have a structure according to Formula 2B

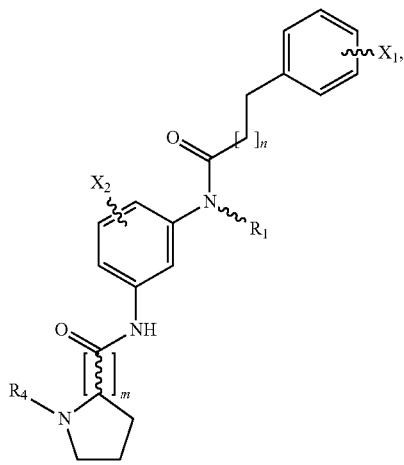

Formula 2B where $X_1$ and $X_2$ can each be independently selected from the group consisting of: H, a $C_1$-$C_5$ unsubstituted or substituted alkyl, a $C_1$-$C_5$ cyclic alkyl where at least 2 carbon atoms of the $C_1$-$C_5$ cyclic alkyl are members of the benzene ring of Formula 2B, an acyl, an amino a sulfono, a chloro, a bromo, a iodo, a flouro, and permissible combinations thereof, where $R_1$ can be a carboxcylic acid or an ester, where $R_4$ can be H, an $C_1$-$C_{10}$ alkyl, an amino, a carboxylic acid, an ester, an amino acid or positively charged derivative thereof, where n can be 1-10, and where m represents the number of carbon atoms in an alkyl, where m can range from 0-10. In some embodiments, the step of contacting can occurs in vitro. In some embodiments, the step of contacting can occur in vivo. The method can further include the step of administering the compound having a structure according to Formula 2 to a subject, wherein the step of administering can occur prior to the step of contacting. In some embodiments, subject suffers from a disease whose pathology can involve a ligand of sortilin or analogue thereof. In some embodiments, the disease can be hypercholesteremia or Alzheimer's disease. In some embodiments, the ligand of sortilin or analogue thereof is PCSK9, apolipoprotein B100, phosphatidylinositides, anionic phospholipids, anionic phospholipids contained on VLDL, amyloid beta, amyloid precursor protein, neurotensin or analogues of neurotensin, lipoprotein lipase, apolipoprotein AV or apolipoprotein E. In some embodiments, the ligand of sortilin or analogue thereof can be an apolipoprotein. In some embodiments the ligand of sortilin or analogue thereof can be PCSK9.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 1A shows a graph demonstrating VLDL-apo B and VLDL-B100 secretion were measured following 18 h incubation of McA cells in cDMEM (black bars) and in 1% BSA/DMEM (gray bars) by immuno slot blotting. FIG. 1B shows a representative standard curve generated from an immuno slot blot (duplicate standards) where VLDL protein is plotted against average chemiluminescence signal in arbitrary units (AU) generated using anti-rat B100 monoclonal antibody and HRP-anti-mouse IgG. FIG. 1C shows representative immunoblots of McA cell lysates from four independent experiments comparing McA cells incubated in cDMEM with 1% BSA/DMEM. Anti-GAPDH blots display equal protein loading. FIG. 1D shows a graph demonstrating relative expression of Apob, Sort1 and Atf3 mRNA in McA cells incubated in 1% BSA/DMEM as a percentage of mRNA present in McA cells incubated in cDMEM. Results are averages from 4 independent experiments.* Indicates means are significantly different.

(FIG. 2A) Following siRNA-mediated KD of sortilin, three clones of McA cells were selected representing high (H, McA60), medium (M, McA62) and low (L, McA53) sortilin expression evaluated by immunoblotting compared with wild type (WT) McA cells. The effect of increasing sortilin KD on VLDL-B100 secretion by McA cells incubated in cDMEM (FIG. 2B) or incubated in 1% BSA/DMEM (FIG. 2C). Results in (FIG. 2B) and (FIG. 2C) are averages of triplicate plates for each condition (n=2 studies). * Indicates means are significantly different from the SCR McA cell line.

(FIG. 3A) Schrödinger's PRIME was run on PDB ID: 4PO7 predicting missing side chains of NT connecting two fragments of the peptide from the crystal structure across the length of the cavity of hsortilin. The predicted peptide XLYENKPRRPYIL generated by connecting C-terminal fragment PYIL-OH and N-terminal fragment XLYEN-OH matches the amino acid sequence for NT and is the right length to connect exactly the N-terminus fitting into site 2 of hsortilin indicated by four of the residues present in the ligand binding diagram of cpd984 generated from the crystal structure. This is depicted in an atomic space filling model and colored yellow and the C-terminal end fitting into site 1 of hsortilin as indicated by the conserved residue R292 (R325 of hsortilin) of crystal structure 4PO7 is depicted in blue. (FIG. 3B) Ligand interaction diagram depicting binding of cpd984 binding to site 2 of hsortilin using Schrödinger's GLIDE indicating key amino acid residues likely to be involved in binding (blue, basic; red, acidic; green, hydrophobic amino acids) including glutamic acids 448 and 542 of pdb ID 4PO7 (Glu481 and Glu 575 of hsortilin). Hydrogen bonds are indicated with purple arrows and pi-stacking are indicated with green arrows. (FIG. 3C) Sensograms showing binding of NT to hsortilin (red, lower curve); cpd984 to hsortilin (green, middle curve) and NT binding in the presence of cpd984 (black, upper curve). The binding response in response units (RU) versus time (sec) was plotted of 100 nM NT injected alone less blank (red 4.5 and 5.5 RU) or with 500 μM cpd984 (blue 64.1 and 64.7 RU) and 500 μM cpd984 alone (green 45.1 and 44.8 RU). Subtracting the averaged RU of NT co-injected with 984 (64.4 RU) from 500 μM cpd984 and 100 nM NT (50.0 RU) results in a 14.5 RU increase in binding to hsortilin. (FIG. 3D) McA cells were incubated in 1% BSA/DMEM containing increasing concentrations of cpd984 for 18 h, and secreted VLDL-B100 was quantified by immuno slot blotting (n=2 studies). * Indicates means differ from the no cpd984 condition. (For interpretation of the references to colour in this figure legend, the reader is referred to the web version of this article.)

(FIG. 4A) McA cell lines with variable sortilin KD were incubated with vehicle (black bars) or with 10 μM cpd984 (gray bars) for 18 h (3-100 mm plates per condition). Viability of McA cells was not compromised by incubations with cpd984 as there was no significant release of LDH into the medium compared with control incubations. VLDL was isolated from media of each plate and VLDL-B100 was quantified by immuno slot blotting. Results presented are averages of the 3 plates ±S.D. (FIG. 4B) McA cells were incubated for 18 h in 1% BSA/DMEM±10 μM cpd984. McA cells were then stimulated with a time course of 250 nM insulin (0, 5, 10 and 15 min). IRβ and AKT, pY-IRβ, and p-AKT (S473) were evaluated by immunoblotting using protein and phospho-specific antibodies.

DETAILED DESCRIPTION

Figure 1A:
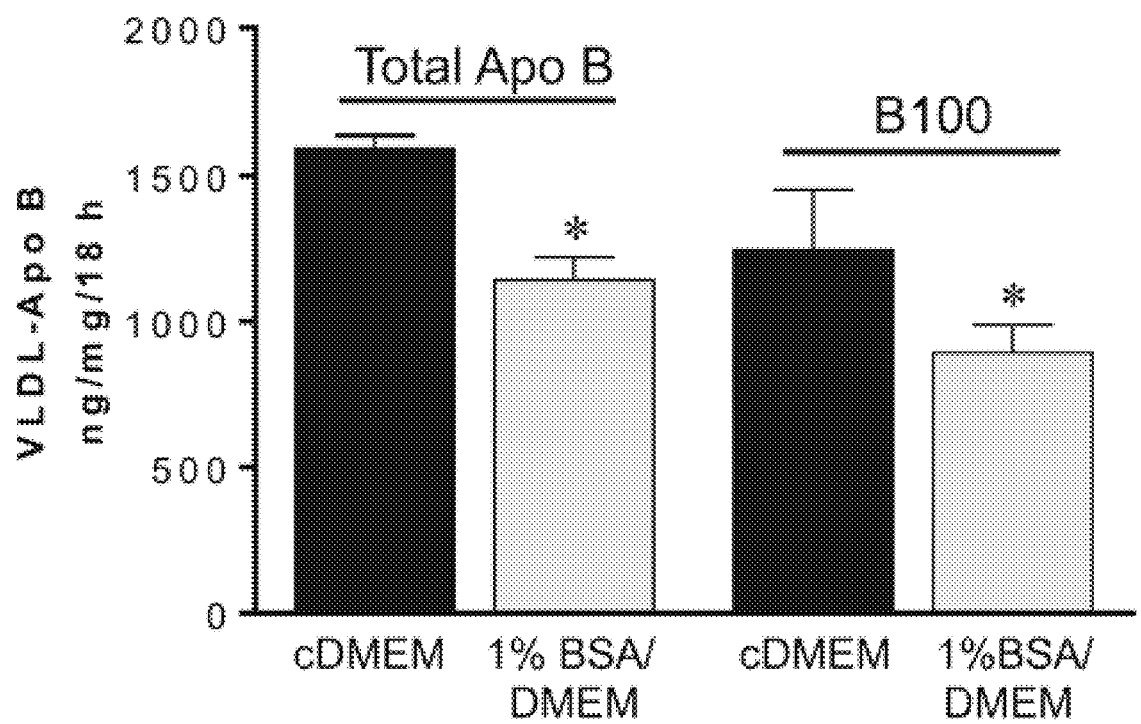
FIGS. 1A-1D show VLDL-apo B secretion and sortilin expression in McA cells.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of biology, molecular biology, microbiology, physiology, organic chemistry, biochemistry, and the like, which are within the skill of the art. Such techniques are explained fully in the literature.

Definitions

As used herein, "about," "approximately," and the like, when used in connection with a numerical variable, can refer to the value of the variable and to all values of the variable that are within the experimental error (e.g., within the 95% confidence interval for the mean) or within +/−10% of the indicated value, whichever is greater.

As used herein, "additive effect" can refer to an effect arising between two or more molecules, compounds, substances, factors, or compositions that is equal to or the same as the sum of their individual effects.

As used herein, "active derivative" and the like can refer to a compound that is capable of binding sortilin or an analogue thereof as provided herein. The term "active derivative" and the like can also refer to a compound or analogue thereof provided herein that can be effective at altering the activity and/or abundance of a protein that is a ligand of sortilin or an anologue thereof, such as PCSK9. The term "active derivative: can also refer to a compound or analogue thereof that can be effective at treating a disease or symptom thereof whose pathology involves a ligand of sortilin or an analogue thereof. Assays for testing the ability of an active derivative to perform in this fashion are known to those of ordinary skill in the art and provided herein. The assays can include, but are not limited to, in vitro and in vivo assays.

As used herein, "administering" can refer to any administration route, including but not limited to, administration that is oral, topical, intravenous, subcutaneous, transcutaneous, transdermal, intramuscular, intra-articular, parenteral, intra-arterial, intradermal, intraventricular, intracranial, intraperitoneal, intralesional, intranasal, rectal, vaginal, by inhalation, or via an implanted reservoir. The term "parenteral" includes subcutaneous, intravenous, intramuscular, intra-articular, intra-synovial, intrasternal, internasal, intrathecal, intrahepatic, intralesional, and intracranial injections or infusion techniques.

As used herein, "attached," "attachment" and the like can refer to the formation of a covalent or non-covalent association (e.g. a bond) between two or more molecules or conjugation of two or more molecules. As used herein, "attached," "attachment" and the like can refer to direct association of two or more molecules together with no intermediate molecules between those that are attached together or to the indirect attachment of two or more molecules together that is mediated via one or more linkers. Where the association is non-covalent, this can encompass charge interactions, affinity interactions, metal coordination, physical adsorption, host-guest interactions, hydrophobic interactions, Π stacking interactions, hydrogen bonding interactions, van der Waals interactions, magnetic interactions, electrostatic interactions, dipole-dipole interactions, and/or combinations thereof. Where the association is covalent, this can encompass bonds where a pair of electrons is shared between one or more atoms in each molecule involved.

As used interchangeably herein, "biocompatible," "biocompatibility," and "biologically compatible" can refer to materials that are, with any metabolites or degradation products thereof, generally non-toxic to the recipient, and cause no significant adverse effects to the recipient.

Generally speaking, biocompatible materials are materials which do not elicit a significant inflammatory or immune response when administered to a patient. In some embodiments, a biocompatible material elicits no detectable change in one or more biomarkers indicative of an immune response. In some embodiments, a biocompatible material elicits no greater than a 10% change, no greater than a 20% change, or no greater than a 40% change in one or more biomarkers indicative of an immune response.

As used herein, "a compound of formula (1), (2), (3), (4), (5), (6), (6a), (6b) (7), (8), (9), (10), (11), (12), (13), (14), (A), (B), (C), (D), and so forth and so on," or "a compound having a structure according to formula (1), (2), (3), (4), (5), (6), (6a), (6b) (7), (8), (9), (10), (11), (12), (13), (14), (A), (B), (C), (D), etc.," compound (1), (2), (3), (4), (5), (6), (6a), (6b) (7), (8), (9), (10), (11), (12), (13), (14), (A), (B), (C), (D), and so forth and so on," or a "compound" can include all or any sub-group of solvates, complexes, polymorphs, derivatives thereof (including but not limited to, radiolabeled derivatives (including deuterated derivatives where one or more H are replaced by D)), tautomers, stereoisomers, and optical isomers of the compound of the formulas listed above and salts thereof.

As used herein, "chemotherapeutic agent" or "chemotherapeutic" can refer to a therapeutic agent utilized to prevent or treat cancer.

As used herein, "control" can refer to an alternative subject or sample used in an experiment for comparison purposes and included to minimize or distinguish the effect of variables other than an independent variable. A control can be positive or negative. One of ordinary skill in the art will appreciate what are appropriate controls for a given context.

As used herein, "concentrated" can refer to an amount of a molecule, compound, or composition, including, but not limited to, a chemical compound, polynucleotide, peptide, polypeptide, protein, antibody, or fragments thereof, that indicates that the sample is distinguishable from its naturally occurring counterpart in that the concentration or number of molecules per volume is greater than that of its naturally occurring counterpart.

As used herein, "derivative" can refer to substituting, deleting, and/or adding one or more atoms or functional groups. The term "derivative" does not mean that the derivative is synthesized from the parent compound either as a starting material or intermediate, although this may be the case. The term "derivative" can include salts, prodrugs, or metabolites of the parent compound. Derivatives include compounds in which free amino groups in the parent compound have been derivatized to form amine hydrochlorides, p-toluene sulfonamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form salts, methyl and ethyl esters, or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imines, thiones, sulfones, tertiary amides, and sulfides. "Derivatives" also includes extensions of the replacement of the cyclopentane ring with saturated or unsaturated cyclohexane or other more complex, e.g., nitrogen-containing rings, and extensions of these rings with various side groups.

As used herein, "diluted" can refer to an amount of a molecule, compound, or composition including but not limited to, a chemical compound, polynucleotide, peptide, polypeptide, protein, antibody, or fragments thereof, that indicates that the sample is distinguishable from its naturally occurring counterpart in that the concentration or number of molecules per volume is less than that of its naturally occurring counterpart.

As used herein, "deoxyribonucleic acid (DNA)" and "ribonucleic acid (RNA)" can generally refer to any polyribonucleotide or polydeoxribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes.

As used herein, "DNA molecule" can include nucleic acids/polynucleotides that are made of DNA.

As used herein, "dose," "unit dose," or "dosage" can refer to physically discrete units suitable for use in a subject, each unit containing a predetermined quantity of a compound as provided herein and/or a pharmaceutical formulation thereof calculated to produce the desired response or responses in association with its administration.

As used herein, "effective amount" can refer to an amount sufficient to effect beneficial or desired results. An effective amount can be administered in one or more administrations, applications, or dosages. "Effective amount" can refer to an amount of a compound, derivative, and/or formulation thereof provided herein that can treat or prevent a disease or symptom thereof whose pathology involves a ligand of sortilin or an analogue thereof. Some diseases include, but are not limited to, whose pathology involves PCSK9, ApoB, binding of anionic phospholipids, binding of anionic phospholipids contained on VLDL, Amyloid Beta, Amyloid precursor protein (APP), neurotensin or analogues of neurotensin, receptor associated protein (RAP), Gal A, amyloid beta-protein, GLUT4 and/or ApoE. In some embodiments, the disease can be cholesterolemia, hypercholesterolemia, hepatic steatosis, diabetes, auto-immune neuroinflammation, Fabry disease, Alzheimer's disease, and combinations thereof. The term "effective amount" can refer to the amount of a compound provided herein to inhibit 5, 10, 15, 20, 25, 30, 35, 40, 45, 50, 55, 60, 65, 70, 75, 80, 85, 90, 95, 97, 98, 99, and/or about 100% or more of the binding of a ligand to sortilin or analogue thereof. The term "effective amount" can refer to the amount of a compound provided herein to inhibit 5, 10, 15, 20, 25, 30, 35, 40, 45, 50, 55, 60, 65, 70, 75, 80, 85, 90, 95, 97, 98, 99, and/or about 100% or more of the binding of a ligand to Site 1 and or Site 2 of sortilin or analogue thereof.

As used herein, "hydrate" can refer to a compound formed by the addition of water. Typically, but not always, this will be crystalline lattice structures that incorporate water molecules. Hydrates include stoichiometric hydrates, as well as compositions containing variable amounts of water.

As used herein, "identity," "identical to", can refer to the relationship between two or more nucleotide or polypeptide sequences, as determined by comparing the sequences. In the art, "identity" also refers to the degree of sequence relatedness between nucleotide or polypeptide as determined by the match between strings of such sequences. "Identity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested.

Methods to determine identity are codified in publicly available computer programs. The percent identity between two sequences can be determined by using analysis software (e.g., Sequence Analysis Software Package of the Genetics Computer Group, Madison Ws.) that incorporates the Needelman and Wunsch, (J. Mol. Biol., 1970, 48: 443-453,) algorithm (e.g., NBLAST, and XBLAST). The default parameters are used to determine the identity for the polypeptides of the present disclosure, unless stated otherwise.

As used herein, "immunomodulator," can refer to an agent, such as a therapeutic agent, which is capable of modulating or regulating one or more immune function or response.

As used herein, "isolated" means separated from constituents, cellular and otherwise, in which the polynucleotide, peptide, polypeptide, protein, antibody, or fragments thereof, are normally associated with in nature. A non-naturally occurring polynucleotide, peptide, polypeptide, protein, antibody, or fragments thereof, do not require "isolation" to distinguish it from its naturally occurring counterpart.

As used herein, "mitigate" can refer to reducing a particular characteristic, symptom, or other biological or physiological parameter associated with a disease or disorder.

The term "molecular weight", as used herein, can generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein, "negative control" can refer to a "control" that is designed to produce no effect or result, provided that all reagents are functioning properly and that the experiment is properly conducted. Other terms that are interchangeable with "negative control" include "sham," "placebo," and "mock."

As used herein, "nucleic acid" and "polynucleotide" generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotide" as that term is intended herein. As used herein, "nucleic acid sequence" and "oligonucleotide" also encompasses a nucleic acid and polynucleotide as defined above.

As used herein "peptide" refers to chains of at least 2 amino acids that are short, relative to a protein or polypeptide.

As used herein, "pharmaceutical formulation" can refer to the combination of an active agent, compound, or ingredient with a pharmaceutically acceptable carrier or excipient, making the composition suitable for diagnostic, therapeutic, or preventive use in vitro, in vivo, or ex vivo.

As used herein "pharmaceutically effective amount", "effective amount" and the like can refer to an amount of a compound, derivative, or formulation thereof provided herein that can treat or prevent a disease or symptom thereof whose pathology involves a ligand of sortilin or an analogue thereof. Some diseases include, but are not limited to, whose pathology involves PCSK9, ApoB, binding of anionic phospholipids, binding of anionic phospholipids contained on VLDL, Amyloid Beta, Amyloid precursor protein (APP), neurotensin or analogues of neurotensin, receptor associated protein (RAP), Gal A, amyloid beta-protein, GLUT4 and/or ApoE. In some embodiments, the disease can be cholesterolemia, Alzheimer's disease, hypercholesterolemia, hepatic steatosis, diabetes, auto-immune neuroinflammation, Fabry disease, and combinations thereof. The term "pharmaceutically effective amount" can refer to the amount of a compound provided herein to inhibit 5, 10, 15, 20, 25, 30, 35, 40, 45, 50, 55, 60, 65, 70, 75, 80, 85, 90, 95, 97, 98, 99, and/or about 100% or more of the binding of a ligand to sortilin or analogue thereof. The term "pharmaceutically effective amount" can refer to the amount of a compound provided herein to inhibit 5, 10, 15, 20, 25, 30, 35, 40, 45, 50, 55, 60, 65, 70, 75, 80, 85, 90, 95, 97, 98, 99, and/or about 100% or more of the binding of a ligand to Site 1 and or Site 2 of sortilin or analogue thereof. In embodiments, the "pharmaceutically effective amount" can be the least amount of a compound, derivative or formulation thereof provided herein needed to treat, prevent, or elicit the desired biological and/or medical effect in the response of a cell, tissue, organ, system, or subject that is being sought by the researcher, veterinarian, medical doctor or other clinician. In some embodiments, the "pharmaceutically effective amount" can be the least amount that can treat or prevent treat or prevent a disease or symptom thereof whose pathology involves a ligand of sortilin or an analogue thereof. Some diseases include, but are not limited to, whose pathology involves PCSK9, ApoB, binding of anionic phospholipids, binding of anionic phospholipids contained on VLDL, Amyloid Beta, Amyloid precursor protein (APP), neurotensin or analogues of neurotensin, receptor associated protein (RAP), Gal A, amyloid beta-protein, GLUT4 and/or ApoE. In some embodiments, the disease can be cholesterolemia, Alzheimer's disease, hypercholesterolemia, hepatic steatosis, diabetes, auto-immune neuroinflammation, Fabry disease, and combinations thereof. The term "pharmaceutically effective amount" can refer to the least amount of a compound, derivative, or formulation thereof provided herein that can inhibit 5, 10, 15, 20, 25, 30, 35, 40, 45, 50, 55, 60, 65, 70, 75, 80, 85, 90, 95, 97, 98, 99, and/or about 100% or more of the binding of a ligand to sortilin or analogue thereof. The term "pharmaceutically effective amount" can refer to the least amount of a compound provided herein to inhibit 5, 10, 15, 20, 25, 30, 35, 40, 45, 50, 55, 60, 65, 70, 75, 80, 85, 90, 95, 97, 98, 99, and/or about 100% or more of the binding of a ligand to Site 1 and or Site 2 of sortilin or analogue thereof. "Pharmaceutically effective amount" or "pharmaceutically effective dose," can refer to the amount of a compound or formulation thereof provided herein that will elicit the biological and/or medical response of a cell, tissue, organ, system, or subject that is being sought by the researcher, veterinarian, medical doctor or other clinician. The pharmaceutically effective amount can vary depending on the compound, formulation the disorder or condition (normal or abnormal) and its severity, the route of administration, time of administration, rate of excretion, drug or compound, judgment of the researcher, veterinarian, medical doctor or other clinician, dosage form, and the age, weight, general health, sex and/or diet of the subject to be treated.

As used herein, "pharmaceutically acceptable" can refer to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration.

As used herein, "pharmaceutically acceptable carrier or excipient" can refer to a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used herein also includes both one and more than one such carrier or excipient. Pharmaceutically acceptable carriers include, but are not limited to, diluents, preservatives, binders, lubricants, disintegrators, swelling agents, fillers, stabilizers, and combinations thereof.

As used herein, "pharmaceutically acceptable salt" can refer to any salt derived from organic and inorganic acids of a compound described herein. Pharmaceutically acceptable salt also refers to a salt of a compound described having an acidic functional group, such as a carboxylic acid functional group, and a base. Pharmaceutically acceptable salt also includes hydrates of a salt of a compound described herein.

As used herein, "positive control" can refer to a "control" that is designed to produce the desired result, provided that all reagents are functioning properly and that the experiment is properly conducted.

As used herein, "protein" as used herein can refer to a molecule composed of one or more chains of amino acids in a specific order. The term protein is used interchangeable with "polypeptide." The order is determined by the base sequence of nucleotides in the gene coding for the protein. Proteins are required for the structure, function, and regulation of the body's cells, tissues, and organs.

As used herein, "purified" or "purify" can be used in reference to a nucleic acid sequence, peptide, or polypeptide that has increased purity relative to the natural environment.

As used herein, "preventative," "preventing," "prevent" and the like can refer to partially or completely delaying and/or precluding the onset or recurrence of a disorder or conditions and/or one or more of its attendant symptoms or barring a subject from acquiring or reacquiring a disorder or condition or reducing a subject's risk of acquiring or reacquiring a disorder or condition or one or more of its attendant symptoms including, but not limited to, malaria, infection and/or transmission of a parasite of the genus *Plasmodium* or a symptom thereof.

As used herein, "purified" or "purify" can be used in reference to a nucleic acid sequence, peptide, or polypeptide that has increased purity relative to the natural environment.

As used herein, "separated" can refer to the state of being physically divided from the original source or population such that the separated compound, agent, particle, chemical compound, or molecule can no longer be considered part of the original source or population.

As used herein, "solvate" refers to a complex of variable stoichiometry formed by a solute (e.g. formulas (1)-(1) (A), (B), (C), (D), or any other compound herein or a salt thereof) and a solvent. Pharmaceutically acceptable solvates may be formed for crystalline compounds wherein solvent molecules are incorporated into the crystalline lattice during crystallization. The incorporated solvent molecules can be water molecules or non-aqueous molecules, such as but not limited to, ethanol, isopropanol, dimethyl sulfoxide, acetic acid, ethanolamine, and ethyl acetate molecules.

As used herein, the term "specific binding" can refer to non-covalent physical association of a first and a second moiety wherein the association between the first and second moieties is at least 2 times as strong, at least 5 times as strong as, at least 10 times as strong as, at least 50 times as strong as, at least 100 times as strong as, or stronger than the association of either moiety with most or all other moieties present in the environment in which binding occurs. Binding of two or more entities may be considered specific if the equilibrium dissociation constant, Kd, is $10^{-3}$ M or less, $10^{-4}$ M or less, $10^{-5}$ M or less, $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less under the conditions employed, e.g., under physiological conditions such as those inside a cell or consistent with cell survival. In some embodiments, specific binding can be accomplished by a plurality of weaker interactions (e.g., a plurality of individual interactions, wherein each individual interaction is characterized by a Kd of greater than $10^{-3}$ M). In some embodiments, specific binding, which can be referred to as "molecular recognition," is a saturable binding interaction between two entities that is dependent on complementary orientation of functional groups on each entity. Examples of specific binding interactions include primer-polynucleotide interaction, aptamer-aptamer target interactions, antibody-antigen interactions, avidin-biotin interactions, ligand-receptor interactions, metal-chelate interactions, hybridization between complementary nucleic acids, etc.

As used interchangeably herein, "subject," "individual," or "patient," can refer to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

The terms "sufficient" and "effective," as used interchangeably herein, can refer to an amount (e.g. mass, volume, dosage, concentration, and/or time period) needed to achieve one or more desired result(s). For example, a therapeutically effective amount refers to an amount needed to achieve one or more therapeutic effects.

As used herein, "synergistic effect," "synergism," or "synergy" can refer to an effect arising between two or more molecules, compounds, substances, factors, or compositions that that is greater than or different from the sum of their individual effects.

As used herein, "therapeutic", "treating", "treat," and the like can refer to include partially or completely delaying, alleviating, mitigating or reducing the intensity of one or more attendant symptoms of a disease or condition including, but not limited to, those involving sortilin or analogue thereof, and/or a ligand of sortilin or analogue thereof.

As used herein, "variant" refers to a polypeptide that differs from a reference polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally. "Variant" includes functional and structural variants.

As used herein, "alkyl" and "alkylene" refer to a saturated hydrocarbon chain having the specified number of member atoms.

The term "alkyl" can also refer to the radical of saturated aliphatic groups (i.e., an alkane with one hydrogen atom removed), including straight-chain alkyl groups, branched-chain alkyl groups, cycloalkyl (alicyclic) groups, alkyl-substituted cycloalkyl groups, and cycloalkyl-substituted alkyl groups. "Alkyl" also refers to a saturated hydrocarbon chain having the specified number of atoms.

The term "alkyl" (or "lower alkyl") as used herein can include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein can refer to an alkyl group, as defined above, but having from one to ten carbons in its backbone structure. Likewise, "lower alkenyl" and "lower alkynyl" have similar chain lengths.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF₃, —CN and the like. Cycloalkyls can be substituted in the same manner.

As used herein, "$C_{1-6}$alkyl" can refer to an alkyl group having any number of member atoms from 1 to 6 member atoms, such as for example 1 to 4 atoms. Other alkyl groups may have any number of member atoms as indicated by the numbers given in the formula, which, like the previous example, can refer to an alkyl group having any number of member atoms within the specified range of member atoms. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl.

As used herein, "heterocyclic group" can refer to a non-aromatic ring and having the specified number of member atoms being saturated or having one or more degrees of unsaturation and, unless otherwise specified, containing one or more heteroatoms.

As used herein, "heteroaryl" can refer to an aromatic ring having the specified number of member atoms and, unless otherwise specified, containing one or more heteroatoms. Bicyclic and other polycyclic ring systems having a heteroaryl ring are described as fused systems.

The term "heteroalkyl," as used herein, can refer to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "heteroalkyl," as used herein, can refer to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

As used herein, "alkoxyl" or "alkoxy," as used herein, can refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl is an ether or resembles an alkoxyl, such as can be represented by one of —O-alkyl, —O-alkenyl, and —O-alkynyl. The terms "aroxy" and "aryloxy", as used interchangeably herein, can be represented by —O-aryl or O-heteroaryl, wherein aryl and heteroaryl are as defined below. The alkoxy and aroxy groups can be substituted as described above for alkyl.

As used herein, "amine" and "amino" (and its protonated form) are art-recognized and refer to both unsubstituted and substituted amines, e.g., a moiety that can be represented by the general formula:

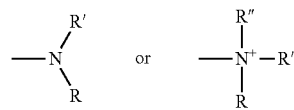

wherein R, R', and R" each independently represent a hydrogen, an alkyl, an alkenyl, —(CH₂)ₘ—R_c or R and R' taken together with the N atom to which they are attached complete a heterocycle having from 4 to 8 atoms in the ring structure; R_c represents an aryl, a cycloalkyl, a cycloalkenyl, a heterocycle or a polycycle; and m is zero or an integer in the range of 1 to 8. In some embodiments, only one of R or R' can be a carbonyl, e.g., R, R' and the nitrogen together do not form an imide. In other embodiments, the term "amine" does not encompass amides, e.g., wherein one of R and R' represents a carbonyl. In further embodiments, R and R' (and optionally R") each independently represent a hydrogen, an alkyl or cycloakly, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R and R' is an alkyl group.

As used herein, "amido" is art-recognized as an amino-substituted carbonyl and includes a moiety that can be represented by the general formula:

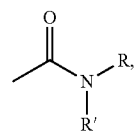

wherein R and R' are as defined above.

As used herein, "Aryl" can refer to $C_5$-$C_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics." The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF₃, —CN, and combinations thereof.

The term "aryl" can also include polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H, 6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. One or more of the rings can be substituted as defined above for "aryl."

As used herein, "aralkyl," can refer to an alkyl group substituted with an aryl group (e.g., an aromatic or heteroaromatic group).

As used herein, "aralkyloxy" can be represented by —O-aralkyl, wherein aralkyl is as defined above.

As used herein, "carbocycle," can refer to an aromatic or non-aromatic ring(s) in which each atom of the ring(s) is carbon.

As used herein, "heterocycle" or "heterocyclic" can refer to a monocyclic or bicyclic structure containing 3-10 ring atoms, and in some embodiments, containing from 5-6 ring atoms, wherein the ring atoms are carbon and one to four heteroatoms each selected from the following group of non-peroxide oxygen, sulfur, and N(Y) wherein Y is absent or is H, O, ($C_1$-$C_{10}$) alkyl, phenyl or benzyl, and optionally containing 1-3 double bonds and optionally substituted with one or more substituents. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbonyl" is art-recognized and includes such moieties as can be represented by the general formula:

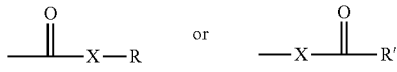

wherein X is a bond or represents an oxygen or a sulfur, and R and R' are as defined above. Where X is an oxygen and R or R' is not hydrogen, the formula represents an "ester". Where X is an oxygen and R is as defined above, the moiety is referred to herein as a carboxyl group, and particularly when R is a hydrogen, the formula represents a "carboxylic acid." Where X is an oxygen and R' is hydrogen, the formula represents a "formate." In general, where the oxygen atom of the above formula is replaced by sulfur, the formula represents a "thiocarbonyl" group. Where X is a sulfur and R or R' is not hydrogen, the formula represents a "thioester." Where X is a sulfur and R is hydrogen, the formula represents a "thiocarboxylic acid." Where X is a sulfur and R' is hydrogen, the formula represents a "thioformate." On the other hand, where X is a bond, and R is not hydrogen, the above formula represents a "ketone" group. Where X is a bond, and R is hydrogen, the above formula represents an "aldehyde" group.

As used herein, "heteroatom" as used herein can refer to an atom of any element other than carbon or hydrogen. Exemplary heteroatoms include, but are not limited to, boron, nitrogen, oxygen, phosphorus, sulfur, silicon, arsenic, and selenium.

As used herein, "nitro" can refer to —$NO_2$; the term "halogen" designates —F, —Cl, —Br, or —I; the term "sulfhydryl" refers to —SH; the term "hydroxyl" refers to —OH; and the term "sulfonyl" refers to —$SO_2$—.

The term "substituted" as used herein, can refer to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, e.g. 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

Heteroatoms, such as nitrogen, can have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc.

As used herein, "suitable substituent" can refer to a chemically and pharmaceutically acceptable group, i.e., a moiety that does not significantly interfere with the preparation of or negate the efficacy of the inventive compounds. Such suitable substituents may be routinely chosen by those skilled in the art. Suitable substituents include but are not limited to the following: a halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, $C_2$-$C_6$ alkynyl, $C_3$-$C_8$ cycloalkenyl, ($C_3$-$C_8$ cycloalkyl)$C_1$-$C_6$ alkyl, ($C_3$-$C_8$ cycloalkyl)$C_2$-$C_6$ alkenyl, ($C_3$-$C_8$ cycloalkyl) $C_1$-$C_6$ alkoxy, $C_3$-$C_7$ heterocycloalkyl, ($C_3$-$C_7$ heterocycloalkyl) $C_1$-$C_6$ alkyl, (C3-$C_7$ heterocycloalkyl)$C_2$-$C_6$ alkenyl, ($C_3$-$C_7$ heterocycloalkyl)$C_1$-$C_6$ alkoxyl, hydroxy, carboxy, oxo, sulfanyl, $C_1$-$C_6$ alkylsulfanyl, aryl, heteroaryl, aryloxy, heteroaryloxy, arylalkyl, heteroaralkyl, arylalkoxy, heteroaralkoxy, nitro, cyano, amino, $C_1$-$C_6$ alkylamino, di-($C_1$-$C_6$ alkyl)amino, carbamoyl, ($C_1$-$C_6$alkyl)carbonyl, ($C_1$-$C_6$ alkoxy)carbonyl, ($C_1$-$C_6$ alkyl)aminocarbonyl, di-($C_1$-$C_6$ alkyl)aminocarbonyl, arylcarbonyl, aryloxycarbonyl, ($C_1$-$C_6$ alkyl)sulfonyl, and arylsulfonyl. The groups listed above as suitable substituents are as defined hereinafter except that a suitable substituent may not be further optionally substituted.

As used herein, "optionally substituted" can indicate that a group may be unsubstituted or substituted with one or more substituents as defined herein.

As used herein, the term "cardiovascular disease" can refer to diseases of large arteries (atherosclerosis). Unless otherwise defined herein, all technical and scientific terms used herein have the same meaning as commonly understood by one of ordinary skill in the art.

Discussion

Sortilin is a membrane glycoprotein that is ubiquitously expressed in many tissues and is most abundant in the central nervous system. Sortilin is involved with protein transport between various cell organelles and can be involved in many biological processes. Therefore, influencing the ability of sortilin to bind its ligands can influence the activity of those ligands. For example, PCSK9 is an enzyme that is ubiquitously expressed in many tissues and cell types and binds to the LDLR. PCSK9 is a ligand for sortilin, where sortilin acts as a secretory chaperone for PCSK9. Thus, sortilin can influence the activity of PCSK9, and amount of the LDLR. Currently, only one ligand binding site on sortilin is known. Sortilin therefore is currently an unexplored potential target for the development of compounds, e.g. small molecules, which are capable of binding sortilin for pharmaceutical development for a variety of diseases.

With that said, described herein are small molecule compounds and formulations thereof that can be capable of binding a first ligand binding site (Site 1) on sortilin or analogue thereof as defined by arginine 325 of SEQ ID NO: 1, or a newly observed second ligand binding site (Site 2) on sortilin or an analogue thereof. Sortilin Site 2 is defined by residues corresponding to SEQ ID NO: 1 present in FIG. 3B: where actual residues of sortilin are 33 residues in number greater than the number provided in the ligand interaction diagram. For example, glutamic acid 448 in the ligand interaction diagram corresponds to glutamic acid 481 of hsortilin and glutamic acid 542 in the ligand interaction diagram of FIG. 3B corresponds to glutamic acid 575 of hsortilin. Also provided herein are methods of altering ligand binding to sortilin by contacting sortilin or an analogue thereof, in vitro or in vivo, with a compound or formulation provided herein. Also provided herein are methods of altering ligand binding to sortilin or an analogue thereof in a subject in need thereof, by administering a compound or formulation thereof provided herein to the subject in need thereof. In some embodiments, the subject in need thereof can be suffering from a disease such as, but not limited to, high cholesterol or Alzheimer's. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Sortilin Binding Compounds and Formulations Thereof

Sortilin Binding Compounds

Provided herein are small molecule compounds that can be capable of binding a ligand binding site on sortilin or an analogue thereof (collectively referred to as "sortilin binding compounds"). Sortilin is a member of the VPS10 family of proteins, which is a family of proteins that share the feature of a VPS10 domain and includes, but is not limited to, Sortilin, SorLA, SorCS1, SorCS2, and SorCS3 (Hampe et al. (2001) Hum. Genet. 108(6):529-536). As used herein, analogues of sortilin include proteins in the VPS10 family as well as structural analogues thereof that contain a binding site similar to the sortilin binding site 1 and/or 2 as described herein. In some embodiments, the sortilin analogue can have an amino acid sequence that can be 70, 75, 80, 85, 90, 95, 97, 98, 99, or about 100% identical to a human sortilin (SEQ ID NOs.: 1-3). In some embodiments, the sortilin analogue is SorLA or a protein having an amino acid sequence that can be 70, 75, 80, 85, 90, 95, 97, 98, 99, or about 100% identical to a human SorLA (SEQ ID NO. 4).

Previously it was known that sortilin had a first ligand binding site (Site 1). As provided in the Examples below, a second site was characterized. Similar sites to sortilin Site 1 capable of binding at least some of the same compounds as sortilin Site 1 have been identified in analogues of sortilin (e.g. SoRLA) (Kitago et al. (2015) Nat. Struct. Mol. Biol. 22:199-206). Provided herein are compounds that can bind to a binding site on sortilin or an analogue thereof. In some embodiments, the binding site can be Site 1 or a structural analogue thereof on sortilin or analogue thereof. In some embodiments, the binding site can be Site 2 or a structural analogue thereof on sortilin or an analogue thereof.

The compound that can bind sortilin or analogue thereof can have a structure according to Formula 1

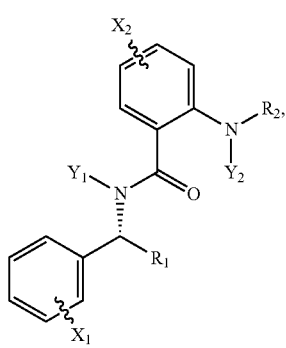

Formula 1 where $X_1$ and $X_2$ can each be independently selected from the group of: H, a $C_1$ to $C_5$ alkyl, a $C_1$ to $C_5$ cyclic alkyl that can be optionally further substituted with a $C_1$ to $C_5$ alkyl and where at least two carbons of the $C_1$ to $C_5$ cyclic alkyl are members of a benzene ring of Formula 1, an acyl, an amino, a sulfono, a chloro, a bromo, a iodo, a flouro, and permissible combinations thereof, where $Y_1$ can be selected from the group of: H, a carboxylic acid or ester thereof, where the ester can be an alkyl ester, where $Y_2$ can be selected from the group of: H, a carboxylic acid or ester thereof, where the ester can be an alkyl ester, where $R_1$ can be a $C_1$-$C_5$ alkyl or a $C_1$-$C_5$ alkene, where $R_2$ can be

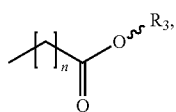

where n can be 1-3 with each carbon being optionally substituted with a $C_1$-$C_5$ alkyl and $R_3$ can be H or a $C_1$ to $C_5$ alkyl, or where $R_2$, together with $Y_2$, can form a tetrazole.

In some embodiments, the compound can have a structure according to Formula 1A

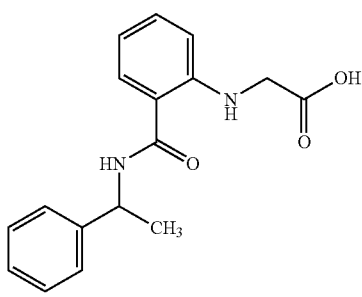

Formula 1A

In some embodiments, the compounds according to Formula 1 and/or Formula 1A can bind Site 1 or a structural analogue thereof on sortilin or analogue thereof. The compound of Formula 1 or 1A can be further optionally substituted with a suitable substituent as desired and as is energetically permissible.

The compound that can bind sortilin or analogue thereof can have a structure according to Formula 2

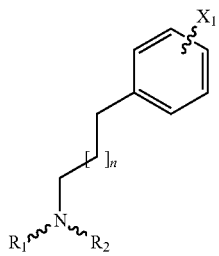

Formula 2 where n can be 1-10, where $X_1$ can be selected from the group of: H, a $C_1$-$C_5$ unsubstituted or substituted alkyl, a $C_1$-$C_5$ cyclic alkyl where at least 2 carbon atoms of the $C_1$-$C_5$ cyclic alkyl are members of the benzene ring of Formula 2, an acyl, an amino a sulfono, a chloro, a bromo, a iodo, a flouro, and permissible combinations thereof, where $R_1$ can be a carboxcylic acid or an ester where $R_2$ can be a 5, 6, or 7 member heterocyclic ring that can be optionally further substituted with a suitable substituent, a sulfonium, a quaternary ammonium,

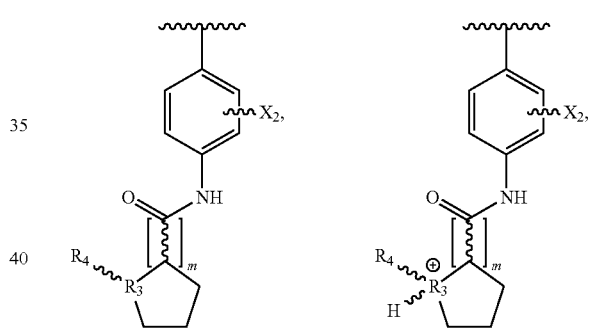

where $X_2$ can be selected from the group of: H, a $C_1$-$C_5$ unsubstituted or substituted alkyl, a $C_1$-$C_5$ cyclic alkyl where at least 2 carbon atoms of the $C_1$-$C_5$ cyclic alkyl are members of the benzene ring of Formula 2, an acyl, an amino a sulfono, a chloro, a bromo, a iodo, a flouro, and permissible combinations thereof, where $R_3$ can be N or S, where $R_4$ can be H, an $C_1$-$C_{10}$ alkyl, an amino, a carboxylic acid, an ester, an amino acid or positively charged derivative thereof, and where m represents the number of carbon atoms in an alkyl, where m can range from 0-10.

In some embodiments, the 5, 6, or 7 member heterocyclic ring that can be optionally substituted with a suitable substituent can be a pyridine, a pyrazole, an imidazole, a pyrrole, a pyrazine, a pyradizine, a pyramidine, or a thiazole. The 5, 6, or 7 member heterocyclic ring that can be optionally substituted with a suitable substituent can be positively charged. In some embodiments, the R4 amino acid can be lysine, arginine, histidine, or a derivative thereof.

The compound that can bind sortilin or analogue thereof can have a structure according to Formula 2A

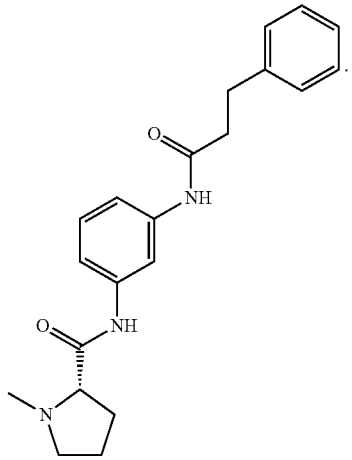

Formula 2A

In some embodiments, the compounds according to Formula 2 and/or Formula 2A can bind Site 2 or a structural analogue thereof on sortilin or analogue thereof.

In some embodiments, the compound can have a structure according to Formula 2B,

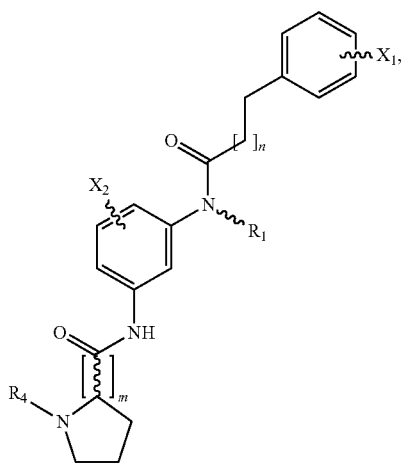

Formula 2B where X1 and X2 can each be independently selected from the group of: H, a C1-05 unsubstituted or substituted alkyl, a C1-C5 cyclic alkyl where at least 2 carbon atoms of the C1-C5 cyclic alkyl are members of the benzene ring of Formula 2B, an acyl, an amino a sulfono, a chloro, a bromo, a iodo, a flouro, and permissible combinations thereof, where R1 can be a carboxcylic acid or an ester, where R4 can be H, an C1-C10 alkyl, an amino, a carboxylic acid, an ester, an amino acid or positively charged derivative thereof, where n can be 1-10, and where m represents the number of carbon atoms in an alkyl, where m can range from 0-10.

In some embodiments of a compound having a structure according to Formula 2B, the R4 amino acid can be lysine, arginine, histidine, or a derivative thereof.

The compound of Formula 2, 2B, and/or 2B can be further optionally substituted with a suitable substituent as desired and as is energetically permissible.

In some embodiments, the compound can be a derivative, including but not limited to, an active derivative of any one of the compounds having a structure according to Formulas 1, 1A, 2, 2A and/or 2B.

The compounds provided herein can compete with binding of a ligand (natural or synthetic) to sortilin or analogue thereof. In some embodiments, the ligand of sortilin or analogue thereof can be PCSK9, apolipoprotein B100, phosphatidylinositides, anionic phospholipids, anionic phospholipids contained on VLDL, amyloid beta, amyloid precursor protein, neurotensin or analogues of neurotensin, lipoprotein lipase, apolipoprotein AV and/or apolipoprotein E. The sortilin binding compounds provided herein can be capable of altering the amount of LDLR present. The sortilin binding compounds can be capable of reducing circulating levels of LDL and/or VLDL in the blood of a subject. The sortilin binding compounds provided herein can be capable of reducing or eliminating interactions of AB particles (e.g. AP-$AB_{1-32}$) in neuronal cells.

The sortilin binding compounds provided herein can be made using techniques and methods generally known to the skilled artisan in view of this disclosure. Such synthesis schemes are within the scope of this disclosure.

Pharmaceutical Formulations

Also provided herein are pharmaceutical formulations that can contain an amount of a compound capable of binding sortilin or an analogue thereof (collectively also referred to as "sortilin binding compounds") as provided elsewhere herein. The sortilin binding compounds described herein can be provided to a subject in need thereof alone or as such as an active ingredient, in a pharmaceutical formulation. In some embodiments, the pharmaceutical formulations contain an effective amount of a sortilin binding compounds. The pharmaceutical formulations described herein can be administered to a subject in need thereof. The subject in need thereof can have a disease or disorder whose pathology involves sortilin or an anologue thereof and/or a ligand of sortilin or an anologue thereof. In some embodiments, the subject can be a human. The term pharmaceutical formulation also encompasses pharmaceutically acceptable salts of the pharmaceutical formulations and/or active ingredients provided herein.

Pharmaceutically Acceptable Carriers and Auxiliary Ingredients and Agents

The pharmaceutical formulations containing an effective amount of a sortilin binding compound described herein can further include a pharmaceutically acceptable carrier. Suitable pharmaceutically acceptable carriers include, but are not limited to, water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active composition.

In addition to the effective amount of a sortilin binding compound described herein, the pharmaceutical formulation can also optionally include an effective amount of an auxiliary active agent, including but not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, chemotherapeutics, antihypertensives, anticoagulants, and antiarrhythmics.

Effective Amounts of the Sortilin Binding Compounds and Auxiliary Agents

The pharmaceutical formulations can contain an effective amount of a sortilin binding compound, and optionally, a therapeutically effective amount of an auxiliary agent. In some embodiments, the effective amount of the sortilin binding compound(s) can range from about 0.3 mg/kg body weight to about 30 mg/kg. The effective amount of the sortilin binding compound(s) can range from about 1 mg to about 10 g. For liquid formulations, some embodiments, the effective amount of the sortilin binding compound(s) or pharmaceutical formulation containing a sortilin binding compound(s) can range from about 10 µL to about 10 mL. One of skill in the art will appreciate that the exact volume will depend on, inter alia, the age and size of the subject, as well as the location of administration. The effective concentration of the sortilin binding compound(s) can range from about 1 nM to 1M.

In embodiments where an optional auxiliary active agent is included in the pharmaceutical formulation, the therapeutically effective amount of the auxiliary active agent will vary depending on the auxiliary active agent. In some embodiments, the therapeutically effective amount of the optional auxiliary active agent can range from 0.001 micrograms to about 1000 milligram. In other embodiments, the therapeutically effective amount of the optional auxiliary active agent can range from about 0.01 IU to about 1000 IU. In further embodiments, the therapeutically effective amount of the auxiliary active agent can range from 0.001 mL to about 1 mL. In yet other embodiments, the therapeutically effective amount of the optional auxiliary active agent can range from about 1% w/w to about 50% w/w of the total pharmaceutical formulation. In additional embodiments, the therapeutically effective amount of the optional auxiliary active agent ranges from about 1% v/v to about 50% v/v of the total pharmaceutical formulation. In still other embodiments, the therapeutically effective amount of the optional auxiliary active agent ranges from about 1% w/v to about 50% w/v of the total pharmaceutical formulation.

Dosage Forms

In some embodiments, the pharmaceutical formulations described herein can be in a dosage form. The dosage forms can be adapted for administration by any appropriate route. Appropriate routes include, but are not limited to, oral (including buccal or sublingual), rectal, epidural, intracranial, intraocular, inhaled, intranasal, topical (including buccal, sublingual, or transdermal), vaginal, intraurethral, parenteral, intracranial, subcutaneous, intramuscular, intravenous, intraperitoneal, intradermal, intraosseous, intracardiac, intraarticular, intracavernous, intrathecal, intravireal, intracerebral, and intracerebroventricular and intradermal. Such formulations can be prepared by any method known in the art.

Dosage forms adapted for oral administration can be discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as foam, spray, or liquid solution. In some embodiments, the oral dosage form can contain about 10 mg to 10 g of a pharmaceutical formulation containing an effective amount or an appropriate fraction thereof of the sortilin binding compound(s). The oral dosage form can be administered to a subject in need thereof by a suitable administration method.

Where appropriate, the dosage forms described herein can be microencapsulated. The dosage form can also be prepared to prolong or sustain the release of any ingredient. In some embodiments, the sortilin binding compound(s) can be the ingredient whose release is delayed. In other embodiments, the release of an optionally included auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, the sortilin binding compound(s), optional auxiliary active ingredient, and/or pharmaceutically acceptable salt thereof can be formulated with a paraffinic or water-miscible ointment base. In other embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the sortilin binding compound(s), the composition containing the sortilin binding compound(s), auxiliary active ingredient, and/or pharmaceutically acceptable salt thereof in a dosage form adapted for inhalation is in a particle-size-reduced form that is obtained or obtainable by micronization. In some embodiments, the particle size of the size reduced (e.g. micronized) compound or salt or solvate thereof, is defined by a D50 value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient, which may be generated by various types of metered dose pressurized aerosols, nebulizers, or insufflators.

In some embodiments, the dosage forms are aerosol formulations suitable for administration by inhalation. In some of these embodiments, the aerosol formulation contains a solution or fine suspension of the sortiilin binding compound(s) and/or pharmaceutically acceptable salt thereof, and a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of the sortilin binding compound(s) or a pharmaceutical formulation thereof. In further embodiments, the aerosol formulation also contains co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses or more are delivered each time.

For some dosage forms suitable and/or adapted for inhaled administration, the pharmaceutical formulation is a dry powder inhalable formulation. In addition to the sortilin binding compound(s), an optional auxiliary active ingredient, and/or pharmaceutically acceptable salt thereof, such a dosage form can contain a powder base such as lactose, glucose, trehalose, manitol, and/or starch. In some of these embodiments, the sortilin binding compound(s), optional auxiliary active ingredient, and/or pharmaceutically acceptable salt thereof is in a particle-size reduced form. In further embodiments, a performance modifier, such as L-leucine or another amino acid, cellobiose octaacetate, and/or metals salts of stearic acid, such as magnesium or calcium stearate.

In some embodiments, the aerosol formulations are arranged so that each metered dose of aerosol contains a predetermined amount of an active ingredient, such as the one or more of the sortilin binding compound(s) described herein.

Dosage forms adapted for vaginal administration can be presented as pessaries, tampons, creams, gels, pastes, foams, or spray formulations. Dosage forms adapted for rectal administration include suppositories or enemas.

Dosage forms adapted for parenteral administration and/or adapted for any type of injection (e.g. intravenous, intraocular, intraperitoneal, subcutaneous, intramuscular, intradermal, intraosseous, epidural, intracardiac, intraarticular, intracavernous, intrathecal, intravitreal, intracerebral, and intracerebroventricular) can include aqueous and/or non-aqueous sterile injection solutions, which can contain anti-oxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and resuspended in a sterile carrier to reconstitute the dose prior to administration. Extemporaneous injection solutions and suspensions can be prepared in some embodiments, from sterile powders, granules, and tablets.

Dosage forms adapted for ocular administration can include aqueous and/or non-aqueous sterile solutions that can optionally be adapted for injection, and which can optionally contain anti-oxidants, buffers, bacteriostats, solutes that render the composition isotonic with the eye or fluid contained therein or around the eye of the subject, and aqueous and non-aqueous sterile suspensions, which can include suspending agents and thickening agents.

For some embodiments, the dosage form contains a predetermined amount of the sortilin binding compound(s) per unit dose. In an embodiment, the predetermined amount of the sortilin binding compound(s) is an effective amount of the sortilin binding compound(s). In other embodiments, the predetermined amount of the sortilin binding compound(s) can be an appropriate fraction of the effective amount of the active ingredient. Such unit doses may therefore be administered once or more than once a day. Such pharmaceutical formulations may be prepared by any of the methods well known in the art.

Methods of Using the Sortlin Binding Compounds and Formulations Thereof

The sortilin binding compounds, derivatives, and formulations thereof provided herein can be used to bind sortilin or an analogue thereof, competitively inhibit a ligand (native or synthetic) of sortilin or an analogue thereof, and/or treat and/or prevent a disease whose pathology involves a ligand of sortilin or an analogue thereof. In some embodiments, the disease can be cholesteremia or Alzheimer's disease. In some embodiments, the ligand of sortilin or analogue thereof can be PCSK9, apolipoprotein B100, phosphatidylinositides, anionic phospholipids, anionic phospholipids contained on VLDL, amyloid beta, amyloid precursor protein, neurotensin or analogues of neurotensin, lipoprotein lipase, apolipoprotein AV and/or apolipoprotein E.

Provided herein are methods of inhibiting binding of a ligand to sortilin or analogue thereof that can include the step of contacting sortilin or an analogue thereof with a sortilin binding compound as provided herein. The step of contacting can occur in vitro or in vivo. The method can further include the step of determining binding of the sortilin binding compound to the sortilin or analogue thereof. One of ordinary skill in the art will appreciate ways that binding of sortilin or analogue thereof can be detected and measured.

Also provided herein are methods of inhibiting binding of a ligand to sortilin or analogue thereof and/or methods of treating and/or preventing a disease in a subject in need thereof that can include the step of administering an amount, such as an effective amount, of one or more sortilin binding compounds to the subject. The subject can be suffering from a disease whose pathology involves a ligand of sortilin or an analogue thereof. In some embodiments, the subject in need thereof suffers from cholesteremia and/or Alzheimer's disease. The method can include the step of administering an amount, such as an effective amount of one or more sortilin binding compounds to a subject such that the binding of PCSK9, apolipoprotein B100, phosphatidylinositides, anionic phospholipids, anionic phospholipids contained on VLDL, amyloid beta, amyloid precursor protein, neurotensin or analogues of neurotensin, lipoprotein lipase, apolipoprotein AV and/05 apolipoprotein E to sortilin or analoge thereof is reduced. In some embodiments, the effective amount of the sortilin binding compound(s) administered to the subject in need thereof can inhibit binding of a ligand of sortilin or analogue thereof (including, but not limited to, PCSK9, apolipoprotein B100, phosphatidylinositides, anionic phospholipids, anionic phospholipids contained on VLDL, amyloid beta, amyloid precursor protein, neurotensin or analogues of neurotensin, lipoprotein lipase, apolipoprotein AV and apolipoprotein E.) by 5, 10, 15, 20, 25, 30, 35, 40, 45, 50, 55, 60, 65, 70, 75, 80, 85, 90, 95, 97, 98, 99, and/or about 100%.

In some embodiments, the sortilin binding compounds can be used as a treatment for a cardiovascular disease. Cardiovascular diseases can can occur in high numbers in patients with diabetes and lipoprotein disorders associated with diabetes. This diabetic dyslipidemia can be related to high levels of circulating triglyceride that are carried by very low density lipoproteins (VLDL-B100) which is a precursor of LDL in the circulating. Disorders of VLDL metabolism can also result in accumulation of triglyceride in the liver, a condition known as hepatic steatosis, which can lead to cirrhosis requiring liver transplantation. Hepatic steatosis can also occur in obesity including childhood obesity that is also associated with metabolic syndrome, a component of which, is high levels of blood triglyceride. Compounds having a structure according to formula 2, e.g. Formula 2A, can be a therapeutic agent for reducing hepatic steatosis and cardiovascular disease risk in obese insulin resistant and type 2 diabetic patients. Compounds having a structure according to formula 2, e.g. Formula 2A, can increase hepatic secretion of triglyceride contained in VLDL-B100 particles thereby reducing the liver content of triglyceride. The additional action of compounds having a structure according to formula 2, e.g. Formula 2A, of increasing LDL receptors through competition of compounds having a structure according to formula 2, e.g. Formula 2A, with PCSK9 at Site 2 of sortilin would ameliorate the high triglyceride levels by increasing the clearance of LDL cholesterol through LDL receptors. As compounds having a structure according to formula 2, e.g. Formula 2A, also increases PIP3 binding to site 1, compounds having a structure according to formula 2, e.g. Formula 2A, could also facilitate VLDL clearance by liver through interaction of sortilin at the cell surface.

In some embodiments, the sortilin binding compounds can be used to treat hypercholesteremia in a subject. Patients with hypercholesterolemia, either acquired or genetic, are typically treated with "statins". Familial hypercholesterolemia (genetic), which is resistant to therapy, has been treated in clinical trials with a combination of "statins" and a monoclonal antibody based therapy to reduce circulating PCSK9 levels. The use of compounds having a structure according to Formula 2, e.g. Formula 2A, in all of these patients can therefore provide an alternative approach to lowering LDL cholesterol. The action of compounds having a structure according to Formula 2, e.g. Formula 2A, can be to compete for binding to sortilin with PCSK9 blocking sortilin's chaperone function in secretion. Reduced secretion of PCSK9 can have a similar effect as the documented reduction of LDL cholesterol with the monoclonal antibody derivatives. In addition, compounds having a structure according to Formula 2, e.g. Formula 2A, can have a favorable effect on circulating VLDL-B100 by favoring cellular uptake of PIP3 containing VLDL by surface expressed sortilin receptors. The predominant effect of compounds having a structure according to Formula 2, e.g. Formula 2A, can be in liver where the majority of LDL receptors are expressed and mechanisms are available for disposing of the form of cholesterol taken up by LDL receptors and sortilin receptor.

In some embodiments, the sortilin binding compounds can be used to treat Alzheimer's disease in a subject. Alzheimer's disease is associated with accumulation of amyloid beta in neurons. A necessary pathway for removal of amyloid beta involves apolipoprotein E, a ligand that binds site 1 of sortilin. Increasing removal of amyloid beta and factors associated with amyloid beta including alpha beta dimer can interact with apo E in their removal. Compounds having a structure according to Formula 2, e.g. Formula 2A, can facilitate ligand interaction with sortilin at site 1 and should through interaction with apo E increase clearance of plaque components reducing symptoms. Sortilin is known to be associated with autophagic lysosomal degradation which would be a pathway for eliminating these toxic protein complexes.

In some embodiments, the sortilin binding compounds provided herein that can bind site 2 of sortilin or an analoge thereof can, via binding at site 2 on sortilin or analogue thereof, can alter binding of a compound to site 1 of sortilin. In some embodiments, a sortilin binding compound provided herein can, via binding at site 2 on sortilin or analogue thereof, enhance or increase binding of a compound to site 1 of sortilin or analogue thereof. In some embodiments, the sortilin binding compounds capable of binding site 2 of sortilin or analogue thereof can be used to alter (e.g. increase or enhance) the binding of a compound to site 1 of sortilin.

In some embodiments, the sortilin binding compounds provide herein can be used to to alter the rate and/or amount degredation of one or more intracellular proteins. The interaction of sortilin with a ligand can lead to lysosomal degredation of intracellular proteins via autophagy. This can result in alterations of proteins secreted by the cell. In some embodiments, VLDL secretion can be altered in this manner.

Sortilin can be expressed on the plasma membrane of cells as well as on the membrane of organelles (e.g. the Golgi). By competing with endogenous ligands for sortilin expressed on the plasma membrane, the sortilin binding compounds provided herein can be capable of altering the interaction of plasma membrane expressed sortilin with circulating lipoproteins.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications,

Example 1

Introduction

The role of sortilin in VLDL-B100 secretion is controversial [1], and inconsistencies have been summarized [2,3]. Some studies suggest sortilin serves as a chaperone where sortilin is hypothesized to facilitate secretion of VLDL-B100 [4]. Other studies demonstrate that sortilin inhibits VLDL-B100 secretion by trafficking towards degradation [5]. An obligatory inverse relationship is hypothesized to result in VLDL-B100 hypersecretion when sortilin is reduced under conditions of severe insulin resistance [6]. Understanding sortilin function is important considering that sortilin is involved in LDL metabolism [7], and is associated with cardiovascular disease [8]. Studies using surface plasmon resonance (SPR) indicate that human VLDL and LDL, both B100-containing lipoproteins, bind to sortilin [4,5]. We directly demonstrated enhanced binding of B100 to sortilin with insulin in insulin responsive McArdle RH7777 (McA) cells [9] suggesting the importance of insulin sensitivity in B100 sortilin interaction. Accordingly, the observed inconsistencies in the relationship between sortilin and VLDL-B100 secretion may relate to insulin sensitivity. Culture conditions of McA cells are known to affect insulin signaling and VLDL secretion, and under serum-enriched conditions McA cells are insulin resistant [10]. Using this model we have explored the relationship of cellular sortilin and VLDL-B100 secretion in insulin sensitive McA cells. Under these defined conditions, we show a role for sortilin in facilitating VLDL-B100 secretion. In contrast, in insulin resistant McA cells, VLDL-B100 is secretion is relatively independent of sortilin. Results demonstrate the complexity of sortilin function and the importance of defining metabolic conditions when examining sortilin and VLDL-B100 relationships.

Materials and Methods

Cell Culture, Materials and Reagents.

McArdle RH-7777 cells (McA cells) were cultured as previously described in serum containing complete Dulbecco's Modified Eagle's Medium (cDMEM) [9,10]. To induce insulin sensitivity, McA cells at 50-60% confluency were incubated for 18 h in serum-free media containing DMEM containing 1% (w/v) BSA (1% BSA/DMEM). Human sortilin (hsortilin) (Ser78-Asn755) with C-terminal 6-His tag was from R&D Systems, Inc., (Minneapolis, Minn.). Plasma from fasted Sprague Dawley rats (BioreclamationIVT, Westbury, N.Y.) was used to prepare VLDL apo B standards. Mouse monoclonal antibody to rat B100 was prepared in our laboratory and characterized previously [11]. Rabbit anti-sortilin antibody was from GeneTex (GTX54854, Irvine, Calif.) or from Abcam (ab16640, Cambridge, Mass.). Rabbit anti-p-AKT (9271), rabbit anti-AKT (9272), and rabbit anti-insulin receptor β-subunit (IRβ, 3025) were from Cell Signaling Technology (Danvers, Mass.). Mouse anti-pY Platinum 4G10 was from EMD Millipore (Temecula, Calif.). (Horseradish peroxidase linked donkey anti-rabbit IgG (NA9340), sheep anti-mouse IgG (NXA931) and ECL Prime Western Blotting Detection Reagent (RPN2232) were from GE Healthcare (Buckinghamshire, UK). All other materials and reagents were essentially as described previously [9]. Compound 98,477,898 (2S)-1-methyl-N-{3-[(3-phenylpropanoyl)-amino]phenyl}pyrrolidine-2-carboxamide (cpd984) was obtained from ChemBridge Corp. (San Diego, Calif.). A stock solution of cpd984 (10 mM) was prepared in DMSO, and stored in aliquots at −20° C.

Knockdown of Sortilin in McArdle Cells Using siRNA.

McA cells were transfected using Fugene6 according to manufacturer's protocol (Promega Corp., Madison Wis.) using three different pGIPZ based vectors expressing shRNAi targeting rat Sort1 mRNA (V2LMM_58553, V3LMM_450660, V3LMM_450662), and one scrambled, non-silencing control (GE Healthcare Dharmacon, Lafayette, Colo.). McA cells with sortilin knockdown (KD) were selected using puromycin. Lysates from each cell line were examined by immunoblotting to assess sortilin expression relative to the non-silencing control cells (SCR).

Immunoblotting.

McA cell lysates were prepared and denatured proteins were separated by SDS-PAGE as described previously [10]. Following electrophoretic transfer to PVDF membranes and blocking non-specific binding, membranes were incubated with primary antibodies overnight at 4° C. in blocking buffer. Antibody binding was detected by incubation for 1-2 h at room temperature with species specific secondary HRP-linked antibodies and developed using Amersham™ Prime reagent (GE Healthcare). Insulin signaling to IRβ and AKT were evaluated using nitrocellulose membranes (Bio-Rad) and phosphospecific (pY, p-AKT(Ser473) and mass specific antibodies [12]. Chemiluminescence was measured using the ChemiDocXRS+system (Bio-Rad) and band intensities quantified using Image Lab 3.0.1 software (Bio-Rad).

RNA Isolation and mRNA Quantitation.

Total RNA was extracted using TriZol Reagent (Life Technologies, Grand Island, N.Y.) and mRNA was measured by quantitative polymerase chain reaction after reverse transcription as previously described [10] by the University of Rochester Genomic Research Center. TaqMan® gene expression primer probe sets used for fluorogenic quantification of rat mRNA transcripts were: apoB, Rn01499054; Sort1, Rn01521847, Atf3, Rn00563784 and Rplp0 (ARBP, 36B4), Rn00821065.

Immuno Slot Blotting.

Experimental media were adjusted to 1% (v/v) protease inhibitor cocktail I (EMD Millipore) and to a salt density of 1.019 g/ml by addition of a solution of NaBr (d=1.495 g/ml). VLDL was isolated by ultracentrifugation in a L-70 Ultracentrifuge (Beckman Coulter, Inc., Fullterton, Calif.) using a 50Ti rotor (200,000×g, 18 h, 14° C.). Following centrifugation, the top 1.5-2.0 ml VLDL fraction was removed using a syringe and weighed to determine volume. VLDL samples were applied in triplicate wells (0.2-0.4 ml per well) in a Bio-Dot® SF apparatus (Bio-Rad). Two PVDF membranes were used together for blotting: the top was Immobilon-P (IPVH09120 SF) and the bottom was Immobilin-PSQ (ISEQ09120 SF); both were obtained from EMD Millipore. VLDL apo B standards were prepared from rat plasma VLDL and total apo B (B100 and B48) and B100 content were determined on stained gels following SDS-PAGE separation [13]. VLDL-apo B standards in TBS were slotted in duplicate alongside test samples. After filtration, 0.4 ml of TBS was added as a wash. After final filtration, membranes were air dried, rehydrated in methanol and incubated in TBS then in blocking buffer at 4° C. overnight. At this stage slot blots were evaluated similarly to immunoblotting. After chemiluminescence development and B100 quantitation, slot blots were stripped by incubation in Restore™ PLUS for 15 min at room temperature (Thermo Scientific, Rockford, Ill.) and were reblocked overnight at 4° C. Total apo B (B100 and B48) present in VLDL was then evaluated following incubation with rabbit polyclonal anti-rat apo B. The bottom PVDF membrane was carried through the entire procedure to assure there was no "bleed through" of test samples. VLDL-apo B and VLDL-B100 content were calculated from standard curves generated by VLDL apo B standards. Recovery of rat VLDL added to unspent media averaged 94%±4.9% with a CV of 5.2% (n=6 replicates).

Surface Plasmon Resonance.

Surface plasmon resonance measurements were performed on a Biacore T200 instrument equipped with Ni-NTA sensor chips with ~6800 response units (RU) for hsortilin covalently immobilized to the surface. HBS-DMSO running buffer (10 mM Hepes pH 7.4, 150 mM NaCl, 1% DMSO) was used at a flow rate of 30 μl/min and injections performed with times for association of 90 s, and dissociation of 300 s, followed by injection of buffer to regenerate the hsortilin surface. Binding was expressed in relative RU; the difference in response between the immobilized protein flow cell and the corresponding control flow cell. NT was administered to the chip containing hsortilin at a concentration of 100 nM. NT at the same concentration of 100 nM was then administered in the presence of cpd984.

Computational Modeling and Compound Screening.

Schrödinger's Maestro program (version 9.3.5) was used as the primary graphical user interface and Maestro version 10.2 (Schrödinger, LLC, New York, N.Y.) was used for ligand interaction diagramming. Virtual screening was performed on compounds contained in Chem-Bridge libraries (www.chembridge.com) that were prepared with Schrödinger's LigPrep program [14]. The virtual screening method was performed using Schrödinger's GLIDE software [15] on the hsortilin crystal structure PDB ID: 4PO7 [16]. Compounds were docked using GLIDE at the site where the N-terminal fragment of NT is found in the crystal structure and cpd984 was chosen for biological screening based on its docking score. Schrödinger's PRIME software was used to generate missing side chains and loops of this crystal structure predicting the NT peptide spanning the cavity of hsortilin [17]. LigPrep was used on the N-terminal peptide XLYEN-OH from this crystal structure and it was then docked back into its respective site on the crystal structure. This self-docking task was able to reproduce the X-ray pose for this ligand.

Statistics.

Unless noted, results are expressed as the mean±S.E.M., where n equals the number of independent experiments in which replicate analyses were performed in each experiment. Significant differences were assessed using Student's t-test with p-values≤0.05 being considered significant.

Results and Discussion

Reduced Sortilin Levels Associate with Lower VLDL Apo B Secretion.

Figure 1B:
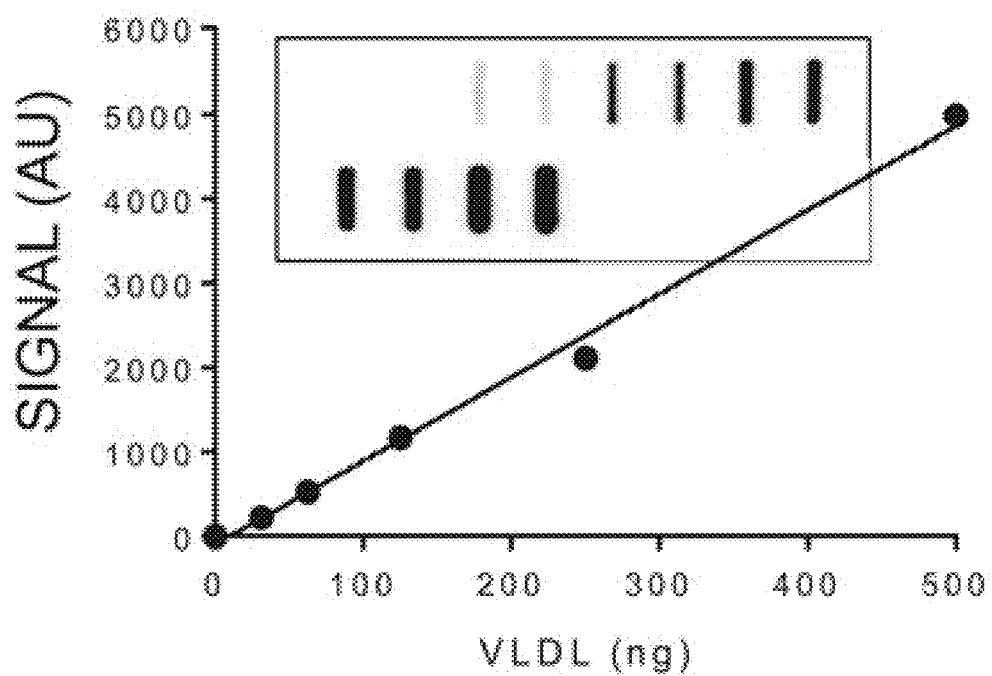
Figure 1C:
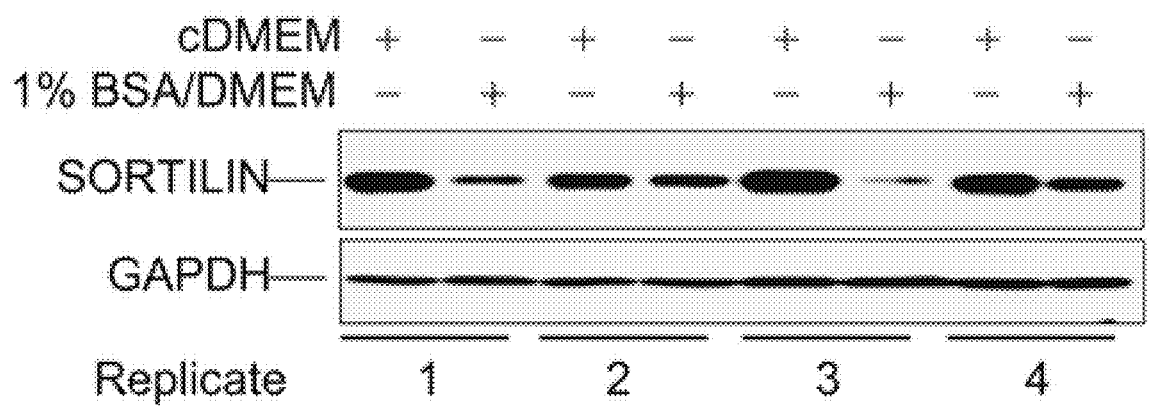
Figure 1D:
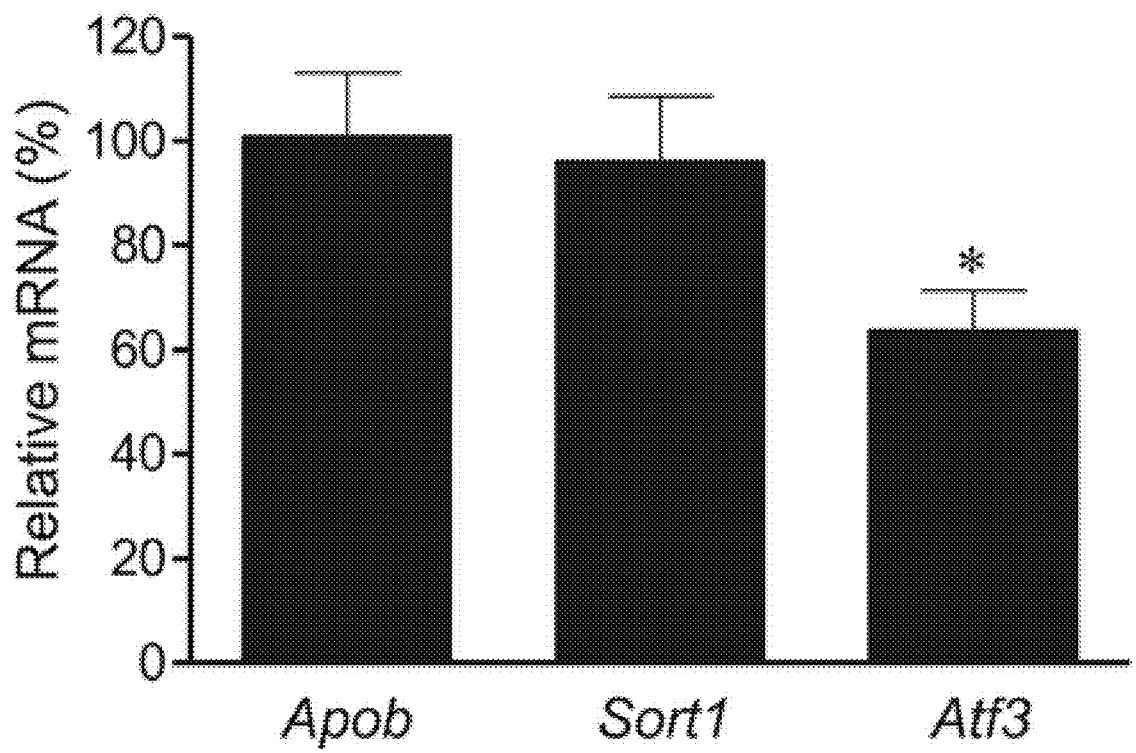

Different levels of media accumulation of apo B by McA cells based on culture conditions have been reported [10]. Under serum enriched conditions (cDMEM), McA cells are insensitive to insulin activation of Class IA phosphatidylinositide 3-kinase (PI3K); insulin dependent translocation of activated PI3K to intracellular membranes, and fail to express insulin dependent apo B degradation (IDAD) [10]. However, following 18 h incubations in 1% BSA/DMEM, insulin sensitivity is restored while total medium apo B concentration is reduced [10]. We extended these results to measurement of VLDL apo B, and specifically to VLDL-B100, the major form of apo B secreted by McA cells [18], and the only form secreted by human liver. Using these conditions, we addressed the extent to which VLDL-apo B secretion was altered (FIG. 1A). Media VLDL-B100 was analyzed by immuno slot blotting following isolation by ultracentrifugation at d<1.019 g/ml (FIG. 1B). Consistent with our previous report, both VLDL-apo B total and VLDL-B100 secretion were significantly reduced in insulin sensitive compared with insulin insensitive McA cells. Secreted VLDL-apo B total (ng/mg/18 h) averaged (mean±SD, n=5): 1595±40 in cDMEM vs 1142±79 in 1% BSA/DMEM. Secreted VLDL-B100 (ng/mg/18 h) averaged (mean±SD, n=5): 1245±208 in cDMEM vs 894±95 in 1% BSA/DMEM. Reduced VLDL secretion was not due to deficiency in fatty acid availability as lipid-enriched BSA was used in the 1% BSA/DMEM medium. Following 1% BSA/DMEM incubation, cellular sortilin levels were significantly depressed (FIG. 1C) averaging only 37%±7% (n=4, p<0.001) of that present in cells incubated in cDMEM. Reduced apo B secretion and cellular sortilin were not the consequence of lowered abundance of mRNA transcripts as Apob and Sort1 mRNA levels were unchanged by culture conditions (FIG. 1D). Considering the suggested role for transcriptional repression of sortilin by the endoplasmic reticulum stress target ATF3 [6], we also measured Atf3 mRNA levels. Atf3 mRNA was reduced on average by 30% in insulin sensitive compared with insensitive McA cells. Decreased ATF3 would be expected to correlate with increased cellular sortilin if there were transcriptional suppression. A corresponding reduction in VLDL-B100 secretion with reduced cellular sortilin suggests a direct relationship. Results are consistent with a model of genetic deletion of sortilin where VLDL-B100 secretion is also reduced [4].

Sortilin KD in Insulin Sensitive McA Cells Associates with Decreased VLDL-B100 Secretion.

Figure 2A:
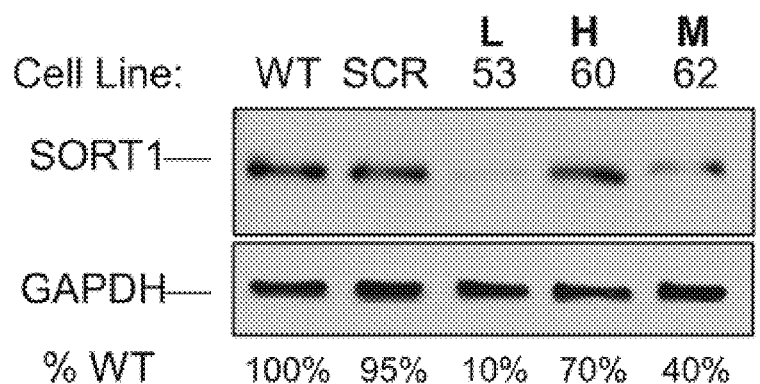
FIGS. 2A-2C show the effect of variable sortilin expression on secretion of VLDL-B100 by McA cells.
Figure 2B:
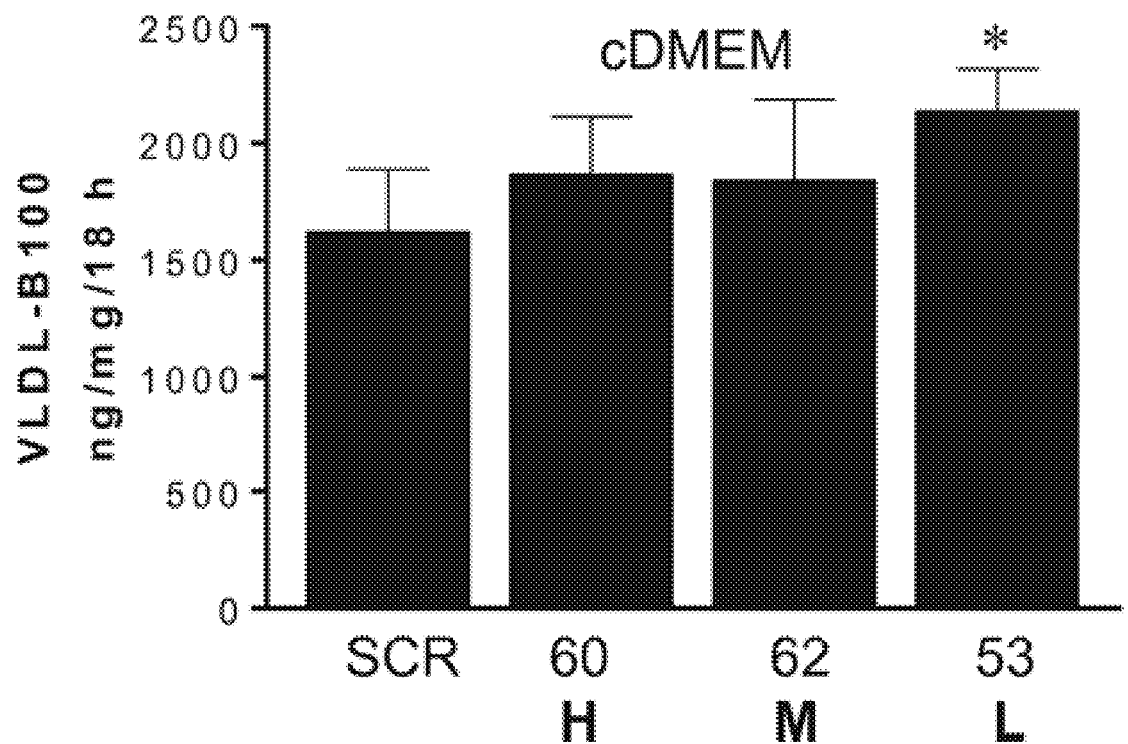
Figure 2C:
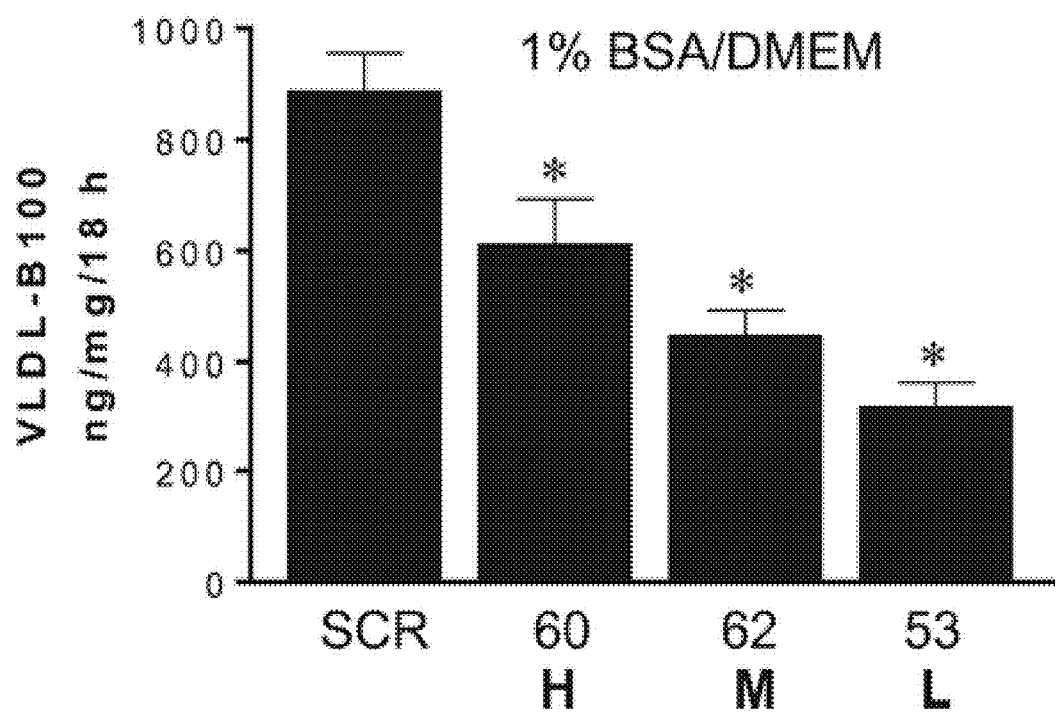

If reduced VLDL-B100 secretion were related to lower cellular sortilin, it would be expected that additional reductions of sortilin would suppress VLDL-B100 even further. To address this premise, three stable cell lines of McA cells using siRNA were prepared with variable KD of sortilin compared with wildtype (WT) and McA cells transfected with scrambled shRNA (SCR) (FIG. 2A). The low (L), medium (M) and high (H) sortilin expressing McA cell lines were incubated in cDMEM, and VLDL-B100 secretion was measured (FIG. 2B). There was no reduction in VLDL-B100 secretion observed with progressively reduced sortilin. There was a small but significant increase in VLDL-B100 secretion in the lowest sortilin expressing McA53 cells (L) compared with SCR that averaged 32% (p<0.05). In contrast, in each McA cell line incubated in 1% BSA/DMEM, there was reduced VLDL-B100 secretion (FIG. 2C). Alterations in the relationship between VLDL-B100 secretion and sortilin under differing culture conditions suggest differences in sortilin function with insulin sensitivity.

Very low density lipoprotein (VLDL) whose integral protein is apolipoprotein B (B100) was studied in a mammalian hepatocyte cell line, McArdle RH7777 (McA), cells, and cellular sortilin expression was examined. Liver cells secrete VLDL-B100 into the blood and therefore the VLDL secreted by these cells represent a relevant human liver model to study the relationships of sortilin to VLDL secretion. It is well known that high levels of VLDL-B100 secretion occur in type 2 diabetes influencing levels of plasma triglyceride and cholesterol which may result in accelerated damage to arteries underlying diseases such as atherosclerosis resulting in heart attacks and stroke. In FIG. 1A, McA cells with enriched conditions (cDMEM) and insulin resistance, demonstrate increased VLDL-B100 and VLDL-total apo B secretion as occurs with humans with insulin resistance and type 2 diabetes. In FIG. 1C, under these same conditions, there are dramatic alterations of sortilin indicating sortilin as a potential target for therapeutic intervention for small molecules as sortilin had been shown to be related to VLDL metabolism. [4] In liver cells sortilin levels can be reduced using molecular techniques involving siRNA, and high (H), middle (M) and low (L) levels of sortilin can be established. Under enriched conditions (cD-MEM) there is little relationship between cellular sortilin and VLDL-B100 secretion (FIG. 2B).

Identification of a Small Molecule that Binds the N-Terminal NT Binding Site on Hsortilin.

Figure 3A:
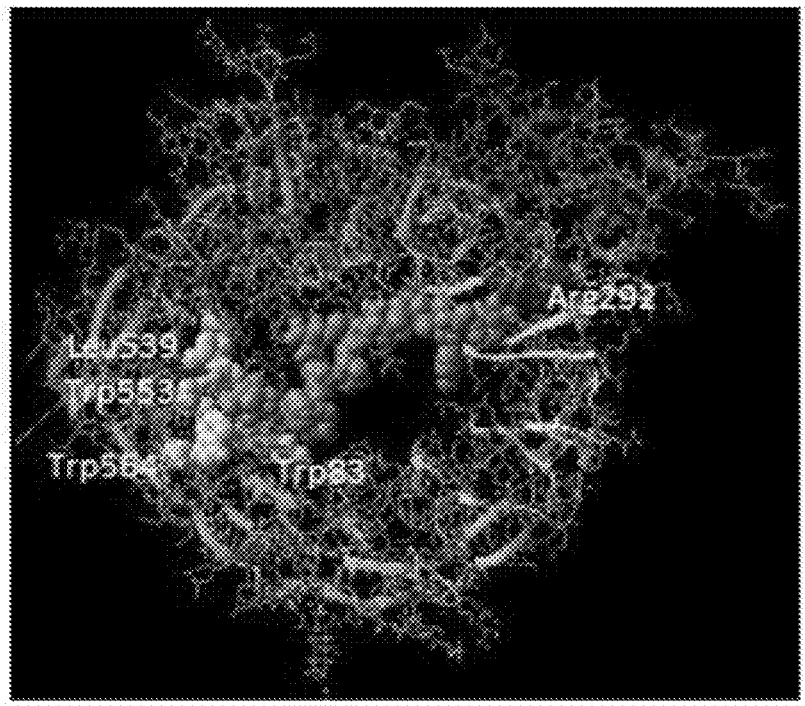
FIGS. 3A-3D show binding characteristics of NT and cpd984 to hsortilin.
Figure 3B:
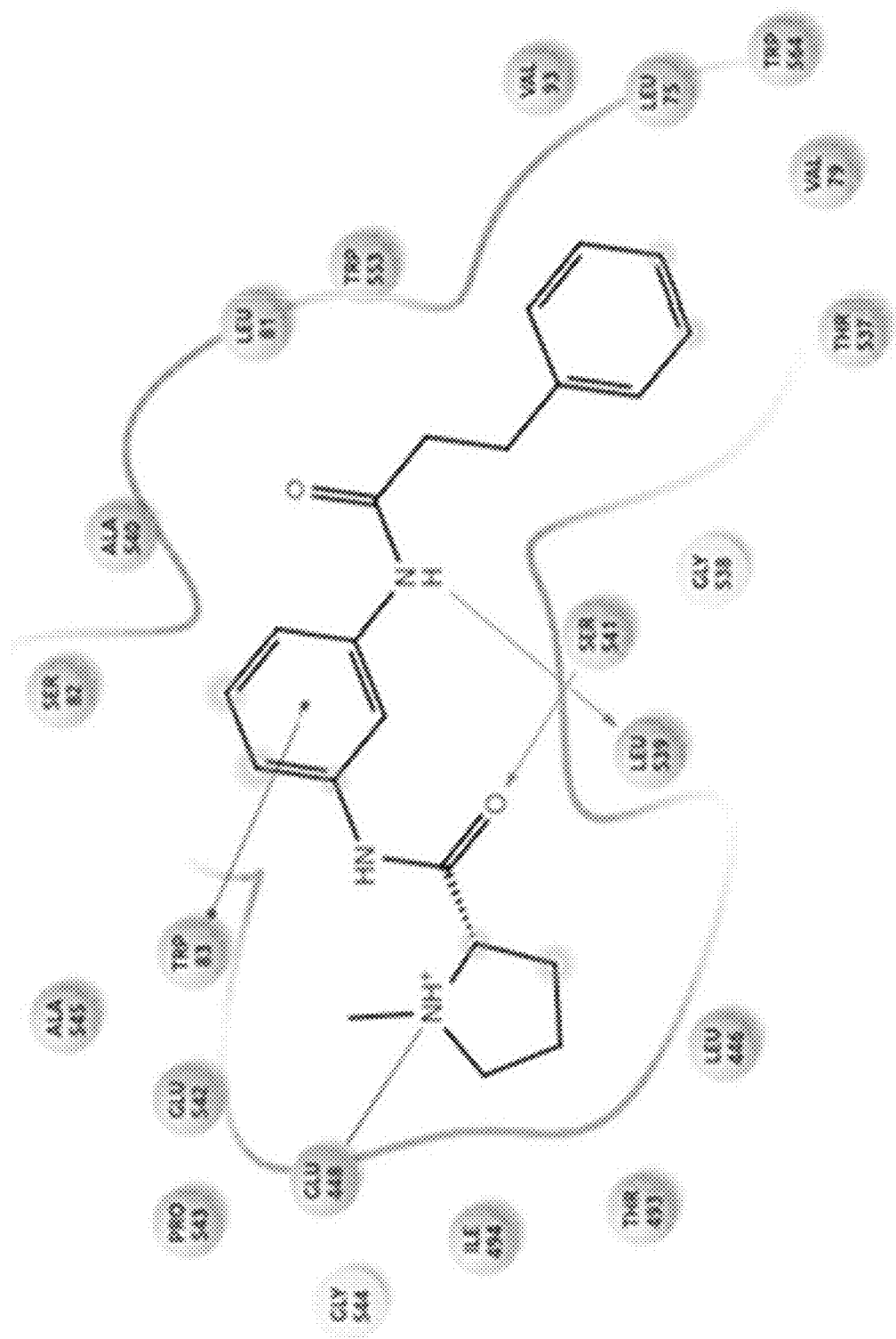

The complexity of sortilin function as a multi-ligand receptor may be related to different sites of ligand binding which direct different functions of sortilin. High resolution crystal structures of hsortilin have been reported, and a C-terminal NT binding site forming a salt bridge between the C-terminal carboxylate of NT and arginine 292 (R292) of the crystal structure has been identified (FIG. 3A) [16]. Small molecules that bind to this site have been characterized [19]. The N-terminus of NT (pyroGlu-Leu-Tyr-Glu-Asn) also interacts with hsortilin [16]. Using Schrödinger software, we explored the N-terminal NT binding site screening compounds from the ChemBridge library and further characterized NT fragments present in the hsortilin crystal structure PDB ID: 4PO7 (FIG. 3A) [16]. We identified cpd984 which had a high predicted affinity to the N-terminal NT binding site using GLIDE XP [15] with a gscore of −9.0 kcal/mol binding strength as compared with a gscore of −8.9 kcal/mol for the N-terminal NT sequence. The position of cpd984 relative to critical amino acid residues of this region is shown (FIG. 3B). Surface amino acids at the binding site for N-terminal NT correspond with amino acids in the interaction diagram presented for cpd984 indicating similar regions of binding. In contrast to the results demonstrated under enriched conditions shown in FIG. 2B, under basal conditions (1% BSA/DMEM), there is a direct relationship between cellular sortilin expression and VLDL-B100 secretion. In FIG. 3B, one such compound (984) is seen interacting with specific residues of sortilin. The primary ligand binding site on sortilin (SITE 1) has been well characterized by arginine 292 in sortilin binding the carboxy-terminal of neurotensin (NT).[16] SITE 2 is defined by interactions with sortilin of N-terminal NT depicted in FIG. 3A by residues 75, 82, 446, 448, 539, 553, and 564. These residues can be seen defining SITE 2 as shown in FIG. 3B and correspond to residues 108. 115, 479, 481, 572, 586, and 597 of hsortilin.

Cpd984 and NT Bind to Hsortilin.

Figure 3C:
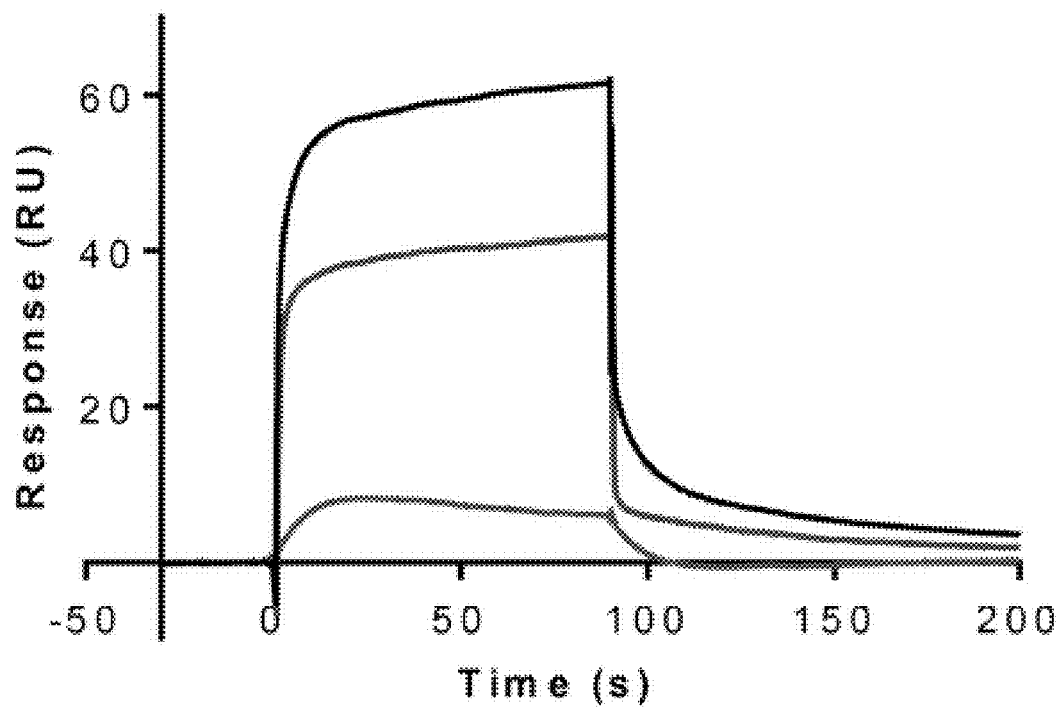

To confirm that cpd984 was bound by hsortilin at a NT-related binding site, we performed SPR (FIG. 3C). We show that individually NT (red, lower curve) and cpd984 (green, middle curve) bind hsortilin. The presence of cpd984 resulted in an increase of 14.5 RU for co-injected NT (black, upper curve) over the RU of the combination of NT and cpd984 alone. Considering the larger size of NT, the increase in RU likely represents enhancement of NT binding to hsortilin by cpd984.

Sortilin is known to influence the fate of VLDL-B100.[5] The complexity of sortilin function has been summarized [1] and may be related to sites of ligand binding that direct different functions. The ectodomain of human sortilin (hsortilin) has been crystallized in the presence of NT, a natural ligand.[20] Using Schrodinger's PRIME, a binding structure for NT has been defined combining the C-terminal (C-term) and N-terminal (N-term) fragments to produce a predicted NT full length binding model. The C-term is the major NT binding site through a salt bridge with arginine 292 (R292) that is defined as SITE 1. The N-term interaction with sortilin is defined as SITE 2, which is a hydrophobic binding site.[21] Schrödinger software was used to identify compounds in the ChemBridge library that bind hsortilin at SITE 1 (54122218 or 541) or SITE 2 (cpd98477898 or 984). VLDL interaction with sortilin at these two sites plays an important role in determining VLDL-B100 secretion or degradation. It is established that 984 binds sortilin by SPR through its ability to compete with NT binding as seen in FIG. 3C. Compounds 541 and 984 are suitable for in vitro cell culture studies and are non-toxic based on LDH release. Compound 984 increases VLDL-B100 secretion by McA cells (FIG. 3D) indicating the utility of this compound binding to SITE 2 and altering a known sortilin function.[21] In FIG. 4A, 984 is seen to enhance the secretion of VLDL-B100 at all concentrations of sortilin which were previously shown to directly relate to VLDL-B100 secretion in FIG. 2C. These results indicate the enhanced ability of 984 to increase VLDL-B100 secretion showing its potential utility as a chaperone to remove VLDL-B100 and its component triglyceride from liver cells as would be useful to ameliorate hepatic steatosis.

PIP3 is shown to bind SITE 1, and while PIP3 binding to SITE 1 increases the potential for VLDL degradation it does this only at higher PIP3 concentrations. Lower PIP3 levels may favor some binding with chaperone activity predominantly being mediated by SITE 2. Supporting evidence for this premise is presented in recent publications.[21],[22] First, it was shown that 984 increases the binding of NT to hsortilin (SITE 1). Second, using diC16-PIP3 liposomes it was demonstrated that 984 shows concentration dependent increases in binding to hsortilin. Third, the binding of the C-term NT (SITE 1) to hsortilin is increased 100-fold when incubated with 984. Fourth, using SPR, 541 (SITE 1) competes for NT binding and 984 enhances NT binding. At higher VLDL PIP3 content following insulin, there is initiation of "sortilin-VLDL-B100-PIP3" complex formation and entry into autophagic-lysosomal degradation. The closer contact of VLDL with sortilin created by SITE 2 favors interaction with PIP3 at SITE 1. Because of the complexity of VLDL structure, diC16-PIP3 nanodiscs[7] were prepared showing competition with NT binding to sortilin which complements studies showing direct competition of diC4-PIP3 liposomes for NT binding.[22] Using diC16 lipoposomes to test binding to sortilin in "pull-down" assays, results indicate that B100 is not required for PIP3 binding. [22] Using PC/PE liposomes as a control, there is specificity for PIP3 for binding. In McA cells under basal conditions, 541 and 984 have opposing dose-dependent effects on the secretion of VLDL-B100. m There is significant enhancement of secretion of VLDL-B100 in McA cells with reduced sortilin at 40% and 10% of control levels by 984. The hypothesis is that the binding of VLDL at SITE 2 enhances the binding to SITE 1 orienting the VLDL in position for further interactions mediated by PIP3. Multiple PIP3 interaction can result in recruitment of additional sortilins anchored in the Golgi membrane distorting the membrane closest to the VLDL particle and initiating autophagy.

Cpd984 Increases VLDL-B100 Secretion by Insulin Sensitive McA Cell.

Figure 3D:
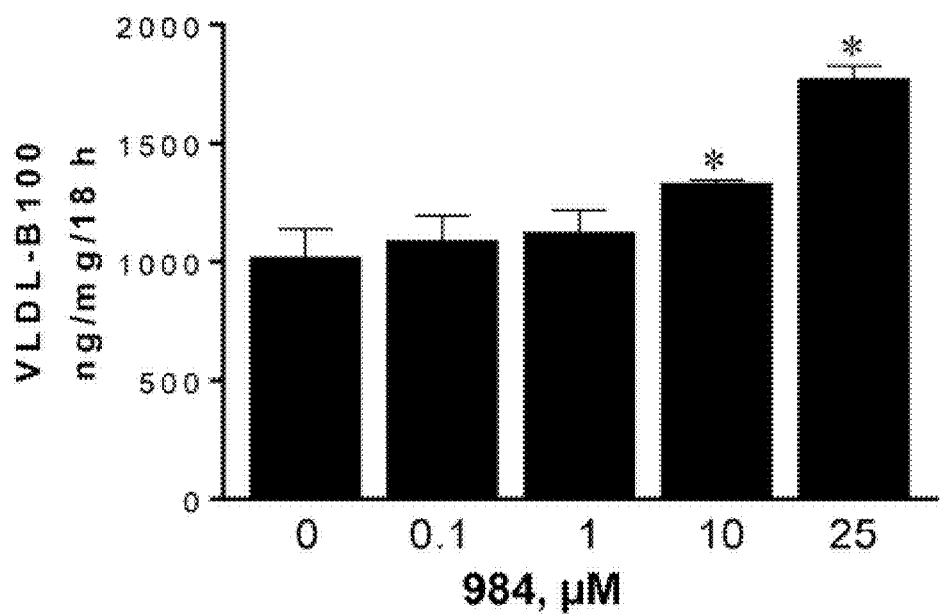
Figure 4A:
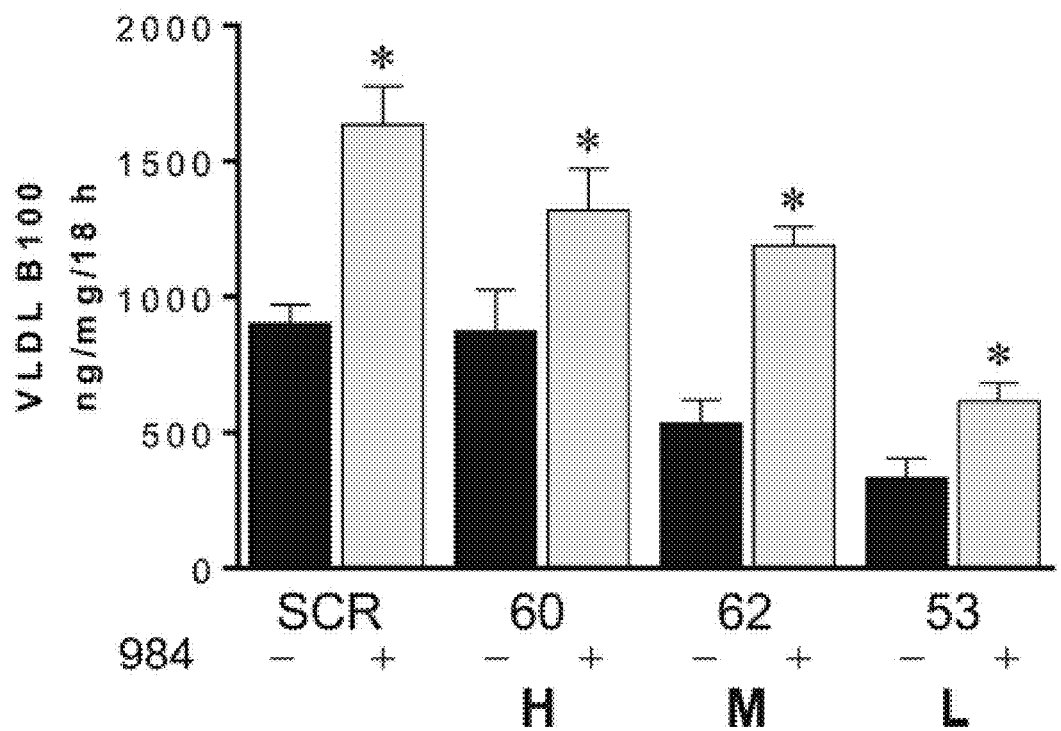
FIGS. 4A-4B shows the effect of cpd984 on VLDL-B100 secretion and on insulin sensitivity in McA cells.

We next tested whether cpd984 alters sortilin function in insulin sensitive McA cells (FIG. 3D). Cpd984 increased VLDL-B100 secretion with significant increases observed at 10 μM and 25 μM averaging 30% and 61%, respectively, over the no cpd984 control.

Cpd984 Increases VLDL-B100 Secretion by McA Cells Under-Expressing Sortilin.

Figure 4B:
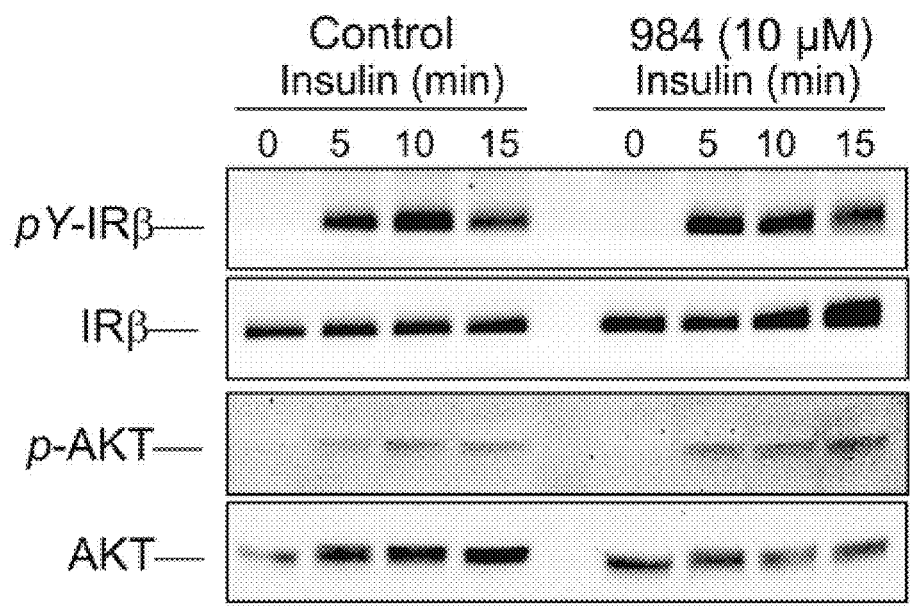

To evaluate the effect of cpd984 on sortilin deficient McA cells, McA cell lines with sortilin KD were incubated with 10 µM cpd984. Cpd984 significantly enhanced VLDL-B100 secretion in each cell line (FIG. 4B). Incubation of McA cells with cpd984 did not alter insulin sensitivity, as insulin-dependent pY of IRβ and stimulation of pAKT(5473) were not affected. Reduced VLDL-B100 secretion occurred in both M (McA62) and L (McA53) cell lines with and without cpd 984 added (p<0.05). Although the mechanism of action of cpd984 is not fully established, its action is likely mediated through interaction with sortilin as although VLDL-B100 secretion is increased, it is still lower with reduced sortilin suggesting sortilin remains rate-limiting. The complex relationship between sortilin and VLDL-B100 secretion is demonstrated in the current study. We show a rate-limiting role for sortilin in VLDL-B100 secretion that is present only in insulin sensitive McA cells and correlates with sortilin expression. Previous studies have shown that binding of B100 to sortilin is enhanced by insulin [9], and precedes B100 degradation mediated by autophagy [12]. With insulin sensitivity, apo B mRNA is unchanged so the decrease in VLDL-B100 secretion observed in 1% BSA/DMEM is likely due to baseline degradation. Together, these data suggest that baseline B100 degradation is further enhanced by insulin which reverses the role of sortilin as a secretory chaperone and directs B100 to autophagy, a pathway seen only with insulin sensitivity. A reasonable explanation for divergent effects of sortilin on VLDL-B100 secretion is the presence of multiple binding sites on sortilin that with binding result in different functions. It is thought that cpd984 may occupy a site on sortilin that enhances VLDL-B100 secretion through the N terminal NT binding domain that favors the chaperone function of sortilin.

Inhibition of the Second Site of Sortilin by Cpd984.

Figures 5A, 5B:
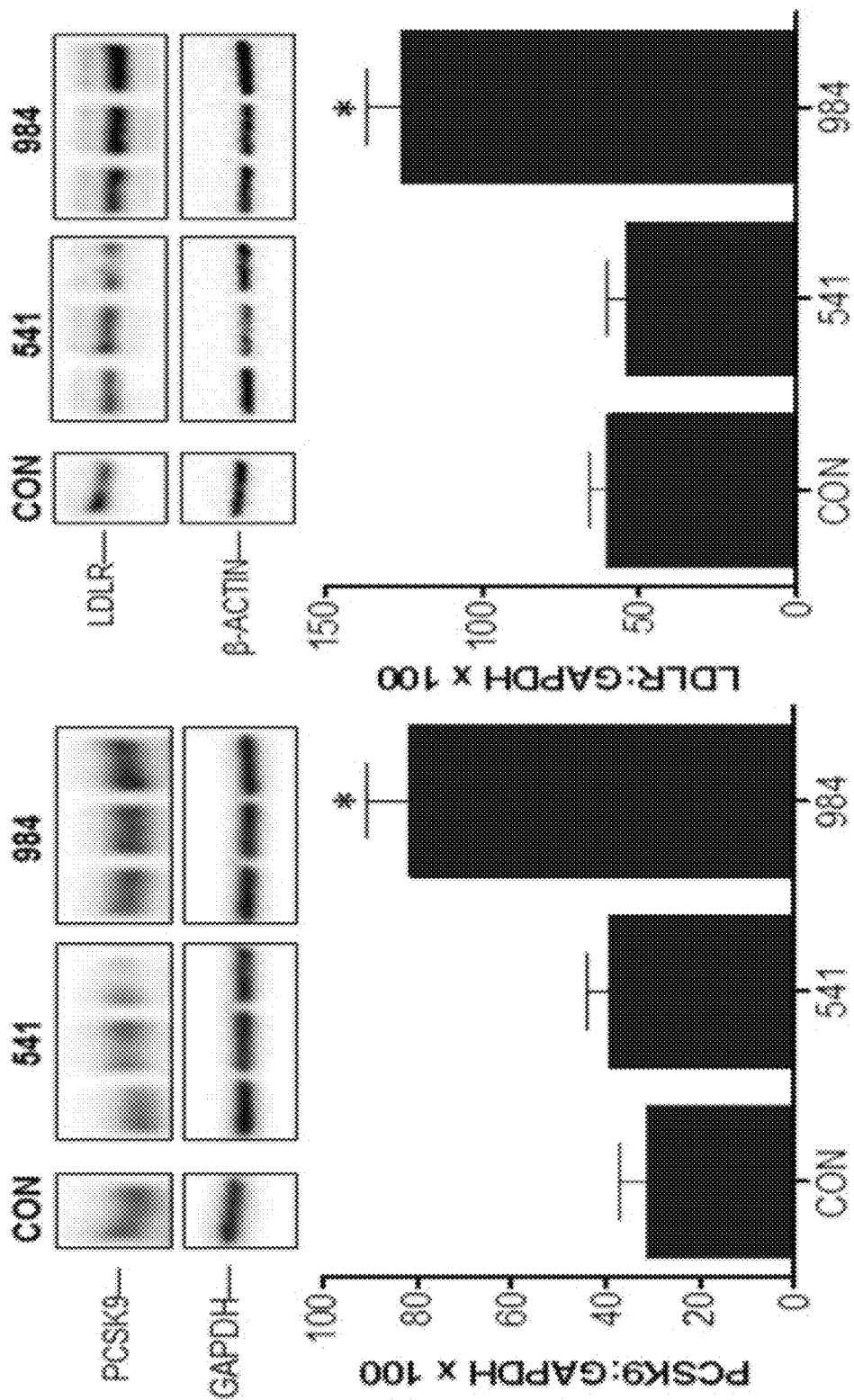
FIGS. 5A-5B demonstrate inhibition of the second site of sortilin by 984. McA cells were incubated in 1% BSA/DMEM with DMSO, 541 (10 μM) or 984 (10 μM) for 18 h. Cellular proteins were extracted and analyzed by IB for LDLR (LS-C146979, 1:2000) (FIG. 5A) or PCSK9 (Ab125251, 1:2000) (FIG. 5B) using HRP-linked secondary antibody and ECL detection. Loading controls included β-ACTIN (Rockland ph600-401-886) and GAPDH (cb1001mAb (6C5). Band intensities were measured using ChemiDocXRS+ system and evaluated using ImageLab 5.1 software (BioRad). Results are average of triplicates ±S.D.

FIGS. 5A-5B demonstrate inhibition of the second site of sortilin by 984. McA cells were incubated in 1% BSA/DMEM with DMSO, 541 (10 µM) or 984 (10 µM) for 18 h. Cellular proteins were extracted and analyzed by IB for LDLR (LS-C146979, 1:2000) (FIG. 5A) or PCSK9 (Ab125251, 1:2000) (FIG. 5B) using HRP-linked secondary antibody and ECL detection. Loading controls included β-ACTIN (Rockland ph600-401-886) and GAPDH (cb1001mAb (6C5). Band intensities were measured using ChemiDocXRS+ system and evaluated using ImageLab 5.1 software (BioRad). Results are average of triplicates ±S.D. PCSK9 is a known ligand for sortilin where sortilin acts as a chaperone for PCSK9 secretion.

Evidence is presented in FIGS. 5A-5B that there is competition for binding by 984 leading to the accumulation of cellular PCSK9. It is likely that SITE 2 represents the binding site for PCSK9 to sortilin as there is no biological difference with administration of 541 that is a SITE 1 binding compound. PCSK9 is known to bind to LDL receptors after it is secreted. PCSK9 bound to LDL receptors results in degradation of LDL receptors that results in higher circulating LDL cholesterol, a risk factor for cardiovascular disease. The increase in LDL receptors observed in FIG. 5B is consistent with reduced PCSK9 secretion. In these experiments, 984 interaction with PCSK9 would be useful in reducing secretion of PCSK9, increasing LDL receptor expression and reducing cardiovascular risk associated with higher concentrations of LDL cholesterol.

Effect of Sortilin Binding Compounds on PIP3 and Treatment of Diseases

Binding of PIP3 to sortilin was documented. PIP3 is a well known downstream signaling molecule for insulin generated through activation of phosphatidylinositde 3-kinase and is a highly negatively charged phospholipid in the class of phosphatidylinositides. PIP3 generation following insulin is reduced in diabetes and conditions of insulin resistance. Increased PIP3 binding induced by 984 can therefore be useful in treatment of diabetic disorders. This can be accomplished through the enhancement of PIP3 binding to sortilin as a result of 984 binding to SITE 2 and enhanced PIP3 binding to SITE 1. Since 984 increases NT binding to sortilin, it is likely that 984 binding to SITE 2 would enhance binding to SITE 1 for other ligands including apoAV, lipoprotein lipase and apo E. Documentation of PIP3 binding to SITE 1 is further secured by competition with NT by diC4-PIP3 as SITE 1 is the major binding site for NT. Relevance for PIP3 in VLDL-B100 binding was determined by showing the presence of PIP3 on circulating VLDL in the blood that is known to contain a monolayer phospholipids including phosphatidylinositides on its surface (data not shown). The presence of PIP3 on VLDL has the potential to alter intravascular metabolism as sortilin is present both intracellularly and also on the cell surface. Further evidence for the enhancement of SITE 2 on the binding of ligands at SITE 1 was evidenced by the observations that 984 increases sortilin binding to PIP3 liposomes (data not shown). 984 was observed to increase liposome binding of sortilin. 984 was observed to increase the binding affinity of the C-terminal NT fragment to immobilized sortilin. Since PIP3 is generated by insulin action, it would be expected that 984 would enhance the interaction of VLDL-B100-PIP3 with sortilin and this would be useful when there is resistance to insulin as occurs with type 2 diabetes.

Summary

Results presented in this Example demonstrate that there is not an obligatory reciprocal relationship between sortilin expression and VLDL B100 secretion, and that the function of sortilin in McA cells depends on insulin sensitivity. Resolution of the controversies related to sortilin and VLDL-B100 secretion may be facilitated by identification of small molecules that bind different sites on sortilin and promote different sortilin function.

Abbreviations Used in Example 1

Apo B, apolipoprotein B; B100, apo B derived from unedited Apob mRNA; IDAD, insulin dependent apolipoprotein B degradation; McA, McArdle RH7777 cells; PI3K, Class IA phosphatidylinositide 3-kinase; SPR, surface plasmon resonance; VLDL, very low density lipoprotein References for Example 1

[1] C. E. Sparks, R. P. Sparks, J. D. Sparks, The enigmatic role of sortilin in lipoprotein metabolism, Curr. Opin. Lipidol. 26 (2015) 598-600.
[2] A. Strong, K. Patel, D. J. Rader, Sortilin and lipoprotein metabolism: making sense out of complexity, Curr. Opin. Lipidol. 25 (2014) 350-357.
[3] M. Kjolby, M. S. Nielsen, C. M. Petersen, Sortilin, encoded by the cardiovascular risk gene SORT1, and its suggested functions in cardiovascular disease, Curr. Atheroscler. Rep. 17 (2015) 496.
[4] M. Kjolby, O. M. Andersen, T. Breiderhoff, A. W. Fjorback, K. M. Pedersen, P. Madsen, P. Jansen, J. Heeren, T. E. Willnow, A. Nykjaer, Sort1, encoded by the cardiovascular risk locus 1p13.3, is a regulator of hepatic lipoprotein export, Cell Metab. 12 (2010) 213-223.
[5] A. Strong, Q. Ding, A. C. Edmondson, J. S. Millar, K. V. Sachs, X. Li, A. Kumaravel, M. Y. Wang, D. Ai, L. Guo, E. T. Alexander, D. Nguyen, S. Lund-Katz, M. C. Phillips, C. R. Morales, A. R. Tall, S. Kathiresan, E. A. Fisher, K. Musunuru, D. J. Rader, Hepatic sortilin regulates both apolipoprotein B secretion and LDL catabolism, J. Clin. Investig. 122 (2012) 2807-2816.

[6] D. Ai, J. M. Baez, H. Jiang, D. M. Conlon, A. Hernandez-Ono, M. Frank-Kamenetsky, S. Milstein, K. Fitzgerald, A. J. Murphy, C. W. Woo, A. Strong, H. N. Ginsberg, I. Tabas, D. J. Rader, A. R. Tall, Activation of E R stress and mTORC1 suppresses hepatic sortilin-1 levels in obese mice, J. Clin. Investig. 122 (2012) 1677-1687.

[7] K. M. Patel, A. Strong, J. Tohyama, X. Jin, C. R. Morales, J. Billheimer, J. Millar, H. Kruth, D. J. Rader, Macrophage sortilin promotes LDL uptake, foam cell formation, and atherosclerosis, Circ. Res. 116 (2015) 789-796.

[8] K. Musunuru, A. Strong, M. Frank-Kamenetsky, N. E. Lee, T. Ahfeldt, K. V. Sachs, X. Li, H. Li, N. Kuperwasser, V. M. Ruda, J. P. Pirruccello, B. Muchmore, L. Prokunina-Olsson, J. L. Hall, E. E. Schadt, C. R. Morales, S. Lund-Katz, M. C. Phillips, J. Wong, W. Cantley, T. Racie, K. G. Ejebe, M. Orho-Melander, O. Melander, V. Koteliansky, K. Fitzgerald, R. M. Krauss, C. A. Cowan, S. Kathiresan, D. J. Rader, From noncoding variant to phenotype via SORT1 at the 1p13 cholesterol locus, Nature 466 (2010) 714-719.

[9] J. M. Chamberlain, C. O'Dell, C. E. Sparks, J. D. Sparks, Insulin suppression of apolipoprotein B in McArdle RH7777 cells involves increased sortilin 1 interaction and lysosomal targeting, Biochem. Biophys. Res. Commun. 430 (2013) 66-71.

[10] J. D. Sparks, A. L. Magra, J. M. Chamberlain, C. O'Dell, C. E. Sparks, Insulin dependent apolipoprotein B degradation and phosphatidylinositide 3-kinase activation with microsomal translocation are restored in McArdle RH7777 cells following serum deprivation, Biochem. Biophys. Res. Commun. 469 (2016) 326-331.

[11] J. D. Sparks, M. Bolognino, P. A. Trax, C. E. Sparks, The production and utility of monoclonal antibodies to rat apolipoprotein B lipoproteins, Atherosclerosis 61 (1986) 205-211.

[12] J. D. Sparks, C. O'Dell, J. M. Chamberlain, C. E. Sparks, Insulin-dependent apolipoprotein B degradation is mediated by autophagy and involves class I and class III phosphatidylinositide 3-kinases, Biochem. Biophys. Res. Commun. 435 (2013) 616-620.

[13] D. V. Chirieac, N. O. Davidson, C. E. Sparks, J. D. Sparks, PI3-kinase activity modulates apo B available for hepatic VLDL production in apobec-1−/− mice, Am. J. Physiol. 291 (2006) G382-G388.

[14] Schrodinger, LigPrep, Schrodinger, Schrodinger, LLC, New York, N.Y., 2014.

[15] T. A. Halgren, R. B. Murphy, R. A. Friesner, H. S. Beard, L. L. Frye, W. T. Pollard, J. L. Banks, Glide: a new approach for rapid, accurate docking and scoring. 2. Enrichment factors in database screening, J. Med. Chem. 47 (2004) 1750-1759.

[16] E. M. Quistgaard, M. K. Groftehauge, P. Madsen, L. T. Pallesen, B. Christensen, E. S. Sorensen, P. Nissen, C. M. Petersen, S. S. Thirup, Revisiting the structure of the Vps10 domain of human sortilin and its interaction with neurotensin, Protein Sci. 23 (2014) 1291-1300.

[17] M. P. Jacobson, D. L. Pincus, C. S. Rapp, T. J. Day, B. Honig, D. E. Shaw, R. A. Friesner, A hierarchical approach to all-atom protein loop prediction, Proteins 55 (2004) 351-367.

[18] E. Kummrow, M. M. Hussain, M. Pan, J. B. Marsh, E. A. Fisher, Myristic acid increases dense lipoprotein secretion by inhibiting apoB degradation and triglyceride recruitment, J. Lipid Res. 43 (2002) 2155-2163.

[19] T. J. Schroder, S. Christensen, S. Lindberg, M. Langgard, L. David, P. J. Maltas, J. Eskildsen, J. Jacobsen, L. Tagmose, K. B. Simonsen, L. C. Biilmann Ronn, I. E. de Jong, I. J. Malik, J. J. Karlsson, C. Bundgaard, J. Egebjerg, J. B. Stavenhagen, D. Strandbygard, S. Thirup, J. L. Andersen, S. Uppalanchi, S. Pervaram, S. P. Kasturi, P. Eradi, D. R. Sakumudi, S. P. Watson, The identification of AF38469: an orally bioavailable inhibitor of the VPS10P family sorting receptor Sortilin, Bioorg. Med. Chem. Lett. 24 (2014) 177-180.

[20] Quistgaard E M, Madsen P, Groftehauge M K, Nissen P, Petersen C M, Thirup S S. Ligands bind to sortilin in the tunnel of a ten-bladed beta-propeller domain. *Nat Struct Mol Biol.* 2009; 16:96-98.

[21] Sparks R P, Guida W C, Sowden M P, Jenkins J L, Starr M L, Fratti R A, Sparks C E, Sparks J D. Sortilin facilitates vldl-b100 secretion by insulin sensitive mcardle rh7777 cells. *Biochemical and biophysical research communications.* 2016; 478:546-552.

[22] Sparks R P, Jenkins J L, Miner G E, Wang Y, Guida W C, Sparks C E, Fratti R A, Sparks J D. Phosphatidylinositol (3,4,5)-trisphosphate binds to sortilin and competes with neurotensin: Implications for very low density lipoprotein binding. Biochemical and biophysical research communications. 2016; 479:551-556.

Example 2

Introduction.

Sortilin is a multi-ligand binding protein with numerous binding partners [1]. Sortilin binds neurotensin (NT) at two sites: the carboxy terminus (C-term) site 1, and the amino terminus (N-term) site 2 [2]. Sortilin also binds 6100-containing very low density lipoprotein (VLDL) and LDL [3,4]. It was previously demonstrated that sortilin facilitates the secretion of VLDL-B100 by insulin-sensitive McArdle RH7777 (McA) cells [5]. It has been further shown that insulin enhances B100 binding to sortilin in McA cells [6] preceding autophagic destruction [7]. Considering the association of sortilin with VLDL binding and with VLDL-B100 degradation in response to insulin, the possibility for insulin-generated phosphatidylinositol (3,4,5)-trisphosphate (PIP3) to interact directly with sortilin was explored. The potential of PIP3 binding to NT defined binding sites on sortilin was tested. The results in this Example demonstrate a role for PIP3 present on VLDL to directly modulate lipoprotein-sortilin interactions.

Materials and Methods.

Materials.

Plasma from fasted Sprague Dawley rats was obtained from BioreclamationIVT, (Westbury, N.Y.) and used to prepare rat lipoproteins. Bovine serum albumin (BSA) (A7285) was from Sigma-Aldrich Corp. (St. Louis, Mo.). The following materials and reagents were obtained from Echelon Biosciences, Inc. (St. Lake City, Utah) including PIP3 PolyPIPosomes (Y-P039); dibutanoyl PIP3 (diC4-PIP3) (P-3904); dipalmitoyl PIP3 (diC16-PIP3) (P-3916); purified anti-PIP3 IgG (Z-P345b), and purified anti-PIP3 IgM (ZP345) monoclonal antibodies. Biotinylated goat anti-mouse IgM and goat serum (GS) were from Jackson ImmunoResearch Labs, Inc. (West Grove, Pa.). Streptavidin-horseradish peroxidase (HRP), HRP-conjugated sheep anti-mouse IgG (NXA931), HRP-conjugated donkey anti-rabbit IgG (NA9340V), ECL™ Prime western blotting detection reagent, CM7 (S series) and NiNTA (S series) sensor chips were from GE Healthcare (Buckinghamshire, UK). Human sortilin (hsortilin) recombinant protein (Ser78-Asp755) with C-terminal 6-His tag was from R&D Systems, Inc. (Minneapolis, Minn.). Neurotensin C-terminal fragment (P—Y-I-L) (C-term NT) was synthesized by Biomatik Corp. (Wilmington, Del.). SuperBlock®, mouse anti-6X HIS monoclonal antibody and 1-Step™ Ultra TMB-ELISA (TMB) were from Thermo Scientific (Rockford, Ill.). Costar® Assay Plates were from Corning, Inc. (Kennebunk, Me.). Rabbit anti-sortilin polyclonal antibody (GTX54854) was from GeneTex, Inc. (Irvine, Calif.). Compound 98477898 (2S)-1-methyl-N-{3-[(3-phenylpropanoyl)-amino]phenyl} pyrrolidine-2-carboxamide (cpd984) was obtained from ChemBridge Corp. (San Diego, Calif.). All other materials and reagents were essentially as described previously [5].

Computational Modeling.

Schrödinger's Maestro program (version 9.3.5) was used as the primary graphical user interface and Release 2015-2: Maestro, version 10.2 (Schrödinger, LLC, New York, N.Y.) was used for ligand interaction diagramming [8]. Docking of diC4-PIP3 on a grid centered at the C-term NT (site1) of hsortilin crystal structure at excess concentration of NT PDB ID: 4PO7 was performed using Schrödinger's Glide software [9] as described [5]. Docking additionally indicated a strong affinity of PIP3 for site 2 of hsortilin.

Surface Plasmon Resonance.

Surface plasmon resonance (SPR) measurements were performed on a Biacore T200 instrument equipped with two separate CM7 sensor chips, one with about 20,000 response units (RU) and another with about 27,000 RU of hsortilin covalently immobilized. HBS running buffer with and without 1% (v/v) DMSO (10 mM HEPES pH 7.4, 150 mM NaCl) was used at a flow rate of 30 µl/min and injections had an association time of 90 s, dissociation time of 300 s, and binding was measured in relative RU or difference in response between the immobilized protein flow cell and the corresponding control flow cell subtracting relevant blank injections of buffer alone [5]. Regeneration buffer of pH 3.0 glycine was injected after each injection for PIP3 nanodiscs and C-term NT flowed in the presence of cpd984. For all other SPR injections, regeneration consisted of injections of running buffer alone. GE BIAcore T200 evaluation software version 3.0 (BIAevaluate) was used to analyze and export results. Full length NT was injected using 2:1 NT dilutions on ~27,000 RU CM7 surface and kinetics fitted using BIAevaluate Langmuir 1:1 binding model using local Rmax exported from BIAevaluate to Microsoft Excel 2016 with fit indicated by the black line. Full length NT was flowed in the presence of diC4-PIP3 diluted directly in running buffer and RU (5 s before injection stop) plotted in GraphPad Prism version 6.05 according to log [inhibitor] versus response [three parameter] model to obtain IC50 of diC4-PIP3 with respect to full length NT. PIP3 containing nanodiscs were flowed at 2:1 dilutions to obtain kinetic data fitted using about 27,000 RU CM7 surface. Kinetic fit generated with BIAevaluate and local Rmax using Langmuir 1:1 binding model exported from BIAevaluate to Microsoft Excel 2016 with fit indicated by the black line. C-term NT was flowed using 2:1 dilutions alone and co-injected with 100 µM cpd984 and steady state Kd obtained for full length NT using RU (45 and 10 s after injection start, respectively) plotted in GraphPad according to One site-Total binding model.

Preparation of PIP3 Nanodiscs.

Lipid composition of nanodiscs consisted of 3.023 µmol dipalmitoyl phosphatidylcholine (PC), 0.098 µmol diC16-PIP3, and 0.78 µmol 1-palmitoyl, 2-oleoyl phosphatidylethanolamine (PE), which were combined, dried, and desiccated overnight. Lipids were then dissolved in 20 mM sodium deoxycholate in TBS (50 mM Tris-HCl, pH 7.4, 150 mM NaCl, 0.02% (w/v) sodium azide) and sonicated. Membrane scaffold protein 1D1 (MSP1D1)) was then added in a ratio of 70:1 lipid to protein and detergent removed with Bio-Beads® SM-2 (Bio-Rad). Nanodiscs were isolated using size exclusion chromatography [10]. Nanodiscs were quantified using a NanoDrop and extinction coefficient of 21,000 I mol$^{-1}$ cm$^{-1}$ for MSP1D1, and the resultant mg/ml divided by two because there are two MSP proteins per nanodisc.

Liposome Floatation Assay.

Unilamellar liposomes containing specific lipid compositions were produced using lipids dissolved in chloroform that were mixed according to mole percentages of 2.6 µmoles total phospholipid [11,12]. Lipids were dried and desiccated overnight followed by incubation with PBS (2.6 ml) for 1 h. Lipids were resuspended by vortexing and disrupted by sonication for 30 min. To measure binding, a liposome floatation assay was used by adding concentrations 50 nM or 100 nM hsortilin to liposomes (150 µl) containing 5% PIP3, 20% PE and 75% PC; 10% PIP3, 20% PE, 70% PC; or 0% PIP3, 80% PC, and 20% PE as described [12,13]. Samples containing 50 nM or 100 nM protein and liposomes in the presence and absence of cpd984 were incubated for 10 min at 30° C. and 630 µl of 1.65 M sucrose/PBS was added. Samples were overlaid with 630 µl of 0.75 M sucrose/PBS, and PBS to the top of the tube and centrifuged (200,000×g, 90 min, 4° C.), and floated liposomes recovered from the 0.75 M sucrose layer. Liposomes at the interface of the top and second fraction were recovered and diluted in 2 ml of PBS and re-isolated by centrifugation (16,000×g, 20 min, 4° C.). 50 µl PBS and 20 µl 5×SDS sample buffer was added to the final liposome pellet. Bound proteins were resolved by SDS-PAGE and detected by western immunoblotting following transfer to PVDF membranes [5].

Assay of Immunoreactive PIP3 on Rat Plasma Lipoproteins.

Plasma VLDL, LDL and high density lipoprotein (HDL) from fasted rats were isolated by sequential density ultracentrifugation as previously described [14]. Immunoreactive PIP3 on plasma lipoproteins was evaluated by enzyme linked immunoassay and by immunoslot blotting. Enzyme linked immunoassay involved coating 96-well multi-well assay plates with 0.1 ml/well diluted lipoprotein or BSA in 0.05 M carbonate/bicarbonate buffer (25 µg protein/mil) overnight at 4° C. Wells were washed three times and post-coated with SuperBlock® for 1 h at room temperature to block non-specific binding. Anti-PIP3 (IgM) diluted in 1% (v/v) GS/TBS was added (1:1000 dilution) and incubated at 4° C. overnight. Wells were washed three times in 1% (v/v) GS/TBS and 0.1 ml biotinylated goat anti-mouse IgM antibody was then added and incubated for 30 min at 37° C. Wells were washed three times in 1% (v/v) GS/TBS and 0.1 ml of streptavidin-HRP in 1% (v/v) GS/TBS was added (1:500) and incubated for 30 min at 37° C. Wells were washed three times in 1% (v/v) GS/TBS and bound HRP was detected by addition of 0.1 ml TMB reagent with incubation at room temperature. Reaction was terminated by addition of 0.1 ml of 2 M sulfuric acid and absorbance was measured at 450 nm using the iMark™ Microplate Reader (Bio-Rad, Hercules, Calif.). The second method employed immunoslot blotting where rat plasma VLDL and LDL from three separate plasma pools were diluted in TBS (2.5-10 µg protein/ml) and slot blotted (200 µl/slot) onto PVDF membranes as previously described [5]. PolyPIPosomes containing PIP3 diluted 1:2000 in PBS were used as positive control. Following filtration, membranes were air dried, quickly rehydrated in methanol, re-incubated in PBS and then incubated in SuperBlock® solution at 4° C. overnight. Afterwards, membranes were incubated in 3% (w/v) BSA/PBS containing anti-PIP3 (IgG) (1:1000) overnight at 4° C. After washing three times in PBS/0.1% Tween 20 (PBST), membranes were incubated in HRP-conjugated sheep anti-mouse IgG in 3% (w/v) BSA/PBS for 90 min. Membranes were washed three times in PBST and then developed using ECL™ Prime western blotting detection reagent. Chemiluminescence was measured using the ChemiDocXRS+ system (Bio-Rad) and band intensities quantified using Image Lab 3.0.1 software (Bio-Rad).

Statistics.

Unless otherwise noted, results are expressed as mean±S.E.M. SPR experiments were analyzed using GE BIAevaluation Software, Microsoft Excel and GraphPad Prism.

Results and Discussion

Sortilin is a PIP3 Binding Protein.

Sortilin binding to NT has been characterized and involves N-term (site 2) and C-term (site 1) binding sites for binding to a single molecule of sortilin [2,15]. A compound was identified with strong theoretical binding to site 2 (cpd984), and in biologic experiments cpd984 incubation increased VLDL-B100 secretion by McA cells [5]. N-term NT was depicted in site 2 located across the central space of sortilin from PIP3 computationally docked into site 1 of hsortilin (data not shown). The theoretical binding of diC4-PIP3 was modeled for binding to site 1 with a docking score (gscore) of −10.3 kcal/mol indicating a high predicted affinity for hsortilin [8]. DiC4-PIP3 is shown binding to site 1 in FIG. 1A with phosphate groups interacting with arginine 292 (R292). The interaction diagram provided in FIG. 5B indicates a number of additional interacting amino acids. To directly test PIP3 binding to sortilin, we prepared PIP3 containing nanodiscs and performed SPR using immobilized hsortilin (data not shown). Nanodiscs were used to simulate PIP3 in membranes or membrane-like surfaces as might be present on VLDL. The Kd for PIP3 nanodiscs was 17 nM. The theoretical prediction of sortilin as a PIP3 binding protein is supported by these results.

PIP3 Competes with NT for Binding to Sortilin.

To determine whether PIP3 binds to sortilin at similar sites as NT, diC4-PIP3 was flowed in the presence of full length NT on immobilized hsortilin and analyzed the response using SPR. In the absence of hsortilin was approximately 290 nM (data not shown). This value is higher than the nM value previously reported using isothermal titration calorimetry [2], potentially because of unproductive cross-linking of hsortilin to the CM7 chip. At 100 nM NT, there was progressive competition for NT-sortilin interaction by diC4-PIP3. An IC50 of approximately 750 nM was obtained for diC4-PIP3 inhibition of full length NT binding to sortilin (data not shown). Structural analysis of a sortilin-related receptor, sorLA, suggests that a site exists similar to site 2 on sortilin that binds mainly hydrophobic ligands [16]. While there was some predicted binding affinity of PIP3 to site 2 of sortilin, it is unlikely to be relevant to sortilin-lipoprotein interaction as hydrophobic components of PIP3 would be anticipated to be embedded within the lipoprotein. Based on the overall data, we hypothesize that sortilin binds PIP3 at a NT related site, with binding most likely occurring at the C-term site 1.

Immunoreactive PIP3 is Present on Circulating Lipoproteins.

Previous studies have demonstrated the presence of phosphatidylinositols on circulating lipoproteins [17]. PIP3 is present in serum bound to albumin [18]. It was tested whether PIP3 might also be present on plasma lipoproteins. Plasma lipoproteins have a surface monolayer of phospholipids that would orient the phosphatidylinositol head group toward the aqueous environment. Qualitative studies were performed where freshly prepared rat plasma VLDL, LDL and HDL were adsorbed to solid phase plastic wells. After blocking non-specific binding, we detected PIP3 using an IgM monoclonal anti-PIP3 antibody. There was three times the immunoreactivity present in VLDL as compared with LDL, HDL or BSA. To confirm these findings, VLDL and LDL were slot blotted and PIP3 immunoreactivity determined using an IgG monoclonal anti-PIP3 antibody (data not shown). Results were compared with slotted PolyPIPisomes containing PIP3 as a positive control. Calculating the relative reactivity per microgram of three separate preparations of rat plasma VLDL and LDL, there was 4.3, 2.5 and 4.0 times more immunoreactivity present in VLDL compared with each matched LDL. These results indicate there is immunoreactive PIP3 on circulating lipoproteins. The presence of lipoprotein PIP3 could influence the interaction of lipoproteins with corresponding cellular receptors including sortilin.

Sortilin Binds PIP3 Liposomes and Binding is Enhanced by a Sortilin Binding Compound.

Using liposome floatation assay, sortilin was shown to bind PIP3 liposomes, but not PC/PE liposomes (data not shown). A sortilin binding compound (cpd984) was developed to bind site 2 [5], and was used to probe PIP3 and C-term NT binding to sortilin. In the presence of increasing concentrations of cpd984, there was increased sortilin binding to PIP3 liposomes without change in binding to PC/PE liposomes (data not shown). The enhanced binding of PIP3 liposomes to sortilin is confirmed using an anti-sortilin antibody (data not shown). A C-terminal NT tetrapeptide (P—Y-I-L) (C-term NT) was used in SPR experiments to examine the effect of cpd984 on site 1 binding to immobilized hsortilin. The C-term NT alone had a Kd of 138 nM. To test the effect of cpd984, the Kd for the C-term NT in the presence of 100 µM cpd984 was determined. The Kd was lowered from 138 nM to 662. These studies indicate cpd984 enhanced the affinity of binding of PIP3 liposomes and C-term NT to sortilin. The use of liposomes as lipoprotein surrogates containing PIP3 to show binding to sortilin is important, as liposomes do not contain other potential sortilin ligands that would be present on VLDL such as B100 and apoE. It is throught that VLDL containing multiple PIP3 molecules on its surface and additional ligands could bind both sites 1 and 2 on sortilin enhancing binding as the size of spherical VLDL is large enough to span the central region of sortilin. Considering the downstream role PIP3 plays in insulin signaling and the enigmatic role sortilin has in VLDL metabolism [19], the finding that sortilin is a PIP3 binding protein could have important implications for VLDL. The presence of PIP3 on VLDL could influence the relative binding of B100 and apoE to various receptors including sortilin. Furthermore, the presence of PIP3 within the secretory pathway on VLDL might affect cell transit if it were demonstrated to modulate sortilin-B100 binding. It appears from these results that there is an interaction between at least two sites on sortilin in response to binding [5]. Because there is such a strong increase with cpd984 in site 1 ligand binding, the data suggest that there could be a conformational change in sortilin similar to that reported for sorLA [16]. In summary, the data support that sortilin is a PIP3 binding protein that could influence VLDL interaction with sortilin based on PIP3 content. Considering PIP3 is a downstream insulin signaling molecule, the demonstration of sortilin binding and presence of PIP3 on VLDL may represent a novel signaling pathway for insulin action.

Abbreviations for Example 2

PIP3, phosphatidylinositol (3,4,5)-trisphosphate; diC4-PIP3, dibutanoyl PIP3; hsortilin, human recombinant sortilin; NT, neurotensin; C-term, carboxy terminus; N-term, amino terminus; SPR, surface plasmon resonance; RU, response units; VLDL, very low density lipoprotein; B100, apolipoprotein B derived from unedited APOB mRNA.

References for Example 2

[1] M. Kjolby, M. S. Nielsen, C. M. Petersen, Sortilin, encoded by the cardiovascular risk gene SORT1, and its suggested functions in cardiovascular disease, Curr. Atheroscler. Rep. 17 (2015) 496.

[2] E. M. Quistgaard, M. S. Groftehauge, P. Madsen, L. T. Pallesen, B. Christensen, E. S. Sorensen, P. Nissen, C. M. Petersen, S. S. Thirup, Revisiting the structure of the Vps10 domain of human sortilin and its interaction with neurotensin, Protein Sci. 23 (2014) 1291-1300.

[3] K. Musunuru, A. Strong, M. Frank-Kamenetsky, N. E. Lee, T. Ahfeldt, K. V. Sachs, X. Li, H. Li, N. Kuperwasser, V. M. Ruda, J. P. Pirruccello, B. Muchmore, L. Prokunina-Olsson, J. L. Hall, E. E. Schadt, C. R. Morales, S. Lund-Katz, M. G. Phillips, J. Wong, W. Cantley, T. Racie, K. G. Ejebe, M. Orho-Melander, O. Melander, V. Koteliansky, K. Fitzgerald, R. M. Krauss, C. A. Cowan, S. Kathiresan, D. J. Rader, From noncoding variant to phenotype via SORT1 at the 1p13 cholesterol locus, Nature 466 (2010) 714-719.

[4] M. Kjolby, O. M. Andersen, T. Breiderhoff, A. W. Fjorback, K. M. Pedersen, P. Madsen, P. Jansen, J. Heeren, T. E. Willnow, A. Nykjaer, Sort1, encoded by the cardiovascular risk locus 1p13.3, is a regulator of hepatic lipoprotein export, Cell Metab. 12 (2010) 213-223.

[5] R. P. Sparks, W. C. Guida, M. P. Sowden, J. L. Jenkins, M. L. Starr, R. A. Fratti, C. E. Sparks, J. D. Sparks, Sortilin facilitates VLDL-B100 secretion by insulin sensitive McArdle RH7777 cells, Biochem. Biophys. Res. Commun. 478 (2016) 546-552.

[6] J. M. Chamberlain, C. O'Dell, C. E. Sparks, J. D. Sparks, Insulin suppression of apolipoprotein B in McArdle RH7777 cells involves increased sortilin 1 interaction and lysosomal targeting, Biochem. Biophys. Res. Commun. 430 (2013) 66-71.

[7] J. D. Sparks, C. O'Dell, J. M. Chamberlain, C. E. Sparks, Insulin-dependent apolipoprotein B degradation is mediated by autophagy and involves class I and class III phosphatidylinositide 3-kinases, Biochem. Biophys. Res. Commun. 435 (2013) 616-620.

[8] Schrödinger, LLC, New York, N.Y. 2014.

[9] T. A. Halgren, R. B. Murphy, R. A. Friesner, H. S. Beard, L. L. Frye, W. T. Pollard, J. L. Banks, Glide: a new approach for rapid, accurate docking and scoring. 2. Enrichment factors in database screening, J. Med. Chem. 47 (2004) 1750-1759.

[10] A. W. Shaw, V. S. Pureza, S. G. Sligar, J. H. Morrissey, The local phospholipid environment modulates the activation of blood clotting, J. Biol. Chem. 282 (2007) 6556-6563.

[11] J. Mima, W. Wickner, Complex lipid requirements for SNARE- and SNARE chaperone-dependent membrane fusion, J. Biol. Chem. 284 (2009) 27114-27122.

[12] G. E. Miner, M. L. Starr, L. R. Hurst, R. P. Sparks, M. Padolina, R. A. Fratti, The central polybasic region of the soluble SNARE (soluble N-ethylmaleimide-sensitive factor attachment protein receptor) Vam7 affects binding to phosphatidylinositol 3-Phosphate by the PX (Phox homology) domain, J. Biol. Chem. 291 (2016) 17651-17663.

[13] K. Matsuoka, Y. Morimitsu, K. Uchida, R. Schekman, Coat assembly directs v-SNARE concentration into synthetic COPII vesicles, Mol. Cell 2 (1998) 703-708.

[14] J. D. Sparks, T. L. Phung, M. Bolognino, J. Cianci, R. Khurana, R. G. Peterson, M. P. Sowden, J. P. Corsetti, C. E. Sparks, Lipoprotein alterations in 10- and 20-week-old Zucker diabetic fatty rats: hyperinsulinemic versus insulinopenic hyperglycemia, Metabolism 47 (1998) 1315-1324.

[15] E. M. Quistgaard, P. Madsen, M. K. Groftehauge, P. Nissen, C. M. Petersen, S. S. Thirup, Ligands bind to Sortilin in the tunnel of a ten-bladed beta-propeller domain, Nat. Struct. Mol. Biol. 16 (2009) 96-98.

[16] Y. Kitago, M. Nagae, Z. Nakata, M. Yagi-Utsumi, S. Takagi-Niidome, E. Mihara, T. Nogi, K. Kato, J. Takagi, Structural basis for amyloidogenic peptide recognition by sorLA, Nat. Struct. Mol. Biol. 22 (2015) 199-206.

[17] M. Dashti, W. Kulik, F. Hoek, E. C. Veerman, M. P. Peppelenbosch, F. Rezaee, A phospholipidomic analysis of all defined human plasma lipoproteins, Sci. Rep. 1 (2011) 139.

[18] D. S. Wang, A. L. Hsu, C. S. Chen, A phosphatidylinositol 3,4,5-trisphosphate analogue with low serum protein-binding affinity, Bioorg. Med. Chem. 9 (2001) 133-139.

[19] C. E. Sparks, R. P. Sparks, J. D. Sparks, The enigmatic role of sortilin in lipoprotein metabolism, Curr. Opin. Lipidol. 26 (2015) 598-600.

Example 3

Figure 6:
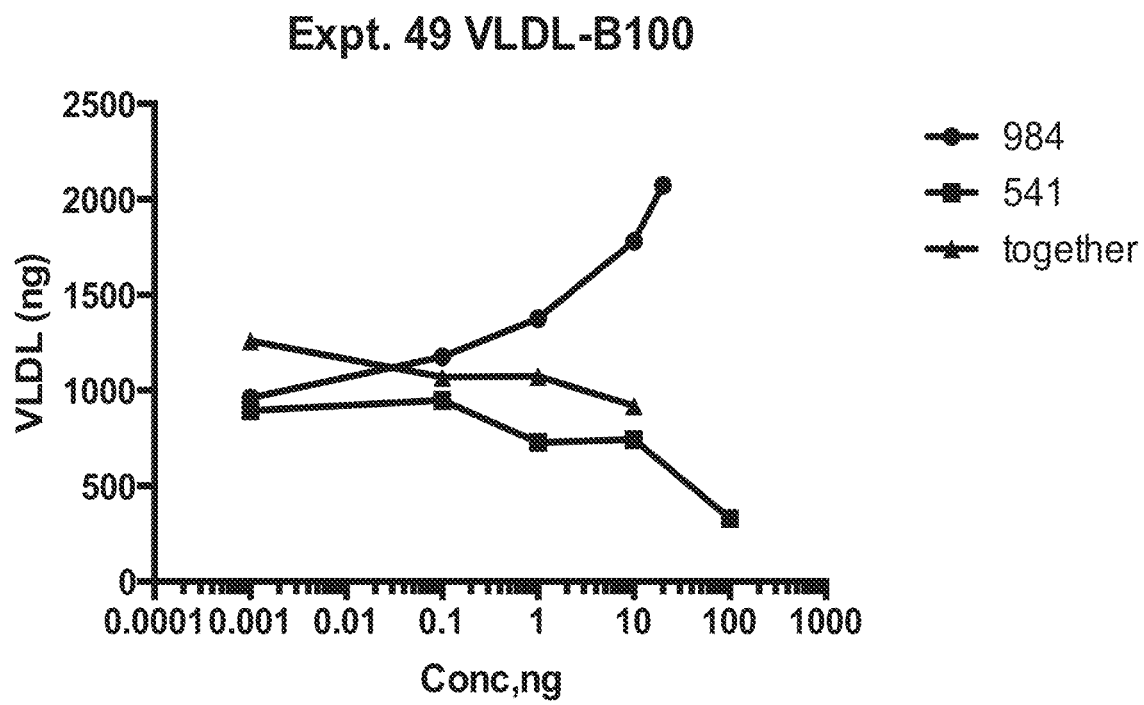
FIG. 6 demonstrates an effect of cpd984 and cpd541 on secretion of VLDL-B100 by hepatocytes. McArdle rat hepatocytes were incubated with increasing concentrations of cpd984 or cpd541 for 14-18 h and media were collected. VLDL (d<0.19 g/ml) was isolated from media by ultracentrifugation and were slotted onto PVDF membranes. After blocking non-specific binding, blots were incubated with monoclonal anti-B100 antibody (24.05) followed by HRP-conjugated anti-mouse IgG. Binding was detected by chemi-luminescence detection and quantified using Bio-Rad software. Results are the average of triplicate analysis in one study.

This Example demonstrates the effect of cpd984 and cpd541 alone and in combination can have an effect on secretion of VLDL-B100 on hepatocytes and VLDL-apo E by hepatocytes. FIG. 6 demonstrates an effect of cpd984 and cpd541 on secretion of VLDL-B100 by hepatocytes. McArdle rat hepatocytes were incubated with increasing concentrations of cpd984 or cpd541 for 14-18 h and media were collected. VLDL (d<0.19 g/ml) was isolated from media by ultracentrifugation and were slotted onto PVDF membranes. After blocking non-specific binding, blots were incubated with monoclonal anti-B100 antibody (24.05) followed by HRP-conjugated anti-mouse IgG. Binding was detected by chemiluminescence detection and quantified using Bio-Rad software. Results are the average of triplicate analysis in one study.

Figure 7A:
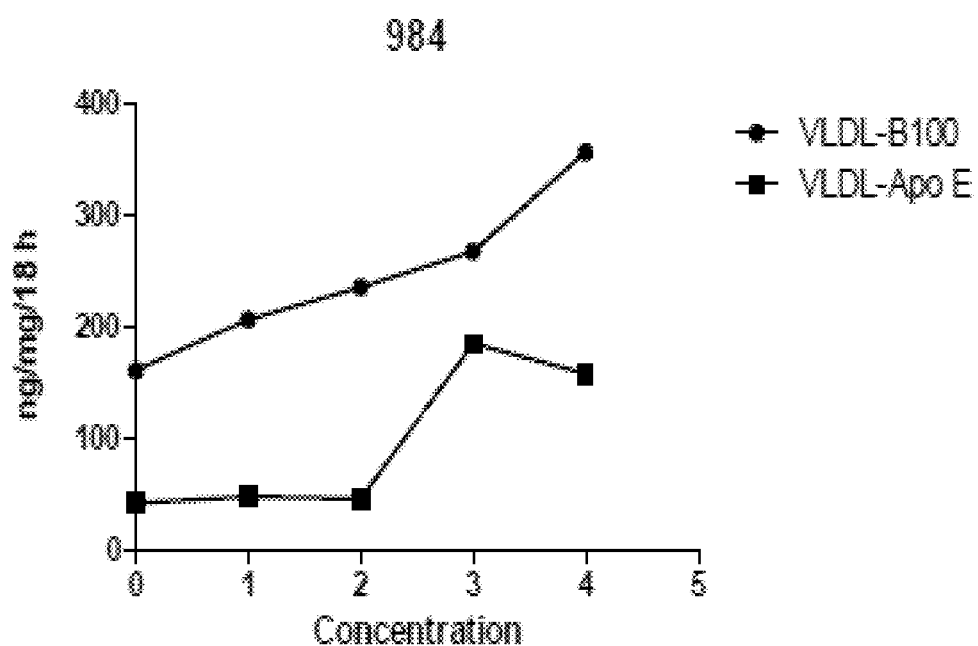
FIGS. 7A-7C show graphs demonstrating an effect of cpd984 and pd541 alone and in combination on the secretion of VLDL-B100 and VLDL-apo E by hepatocytes. McArdle rat hepatocytes were incubated with five media concentrations 0 (no cpd), 1 (0.1 μM), 2 (1 μM), 3 (10 μM) and 4 (25 μM) of cpd984 (FIG. 7A), cpd541 (FIG. 7B), or with a combination of both compounds (FIG. 7C) at indicated concentrations. Hepatocytes were incubated overnight (14-18 h) and media were collected and VLDL-B100 and VLDL-apo E were detected by slot blotting as described above. An anti-rat apoE antibody was used for measurement of VLDL-apo E secretion. Results are the average of triplicate analysis in one study.
Figure 7B:
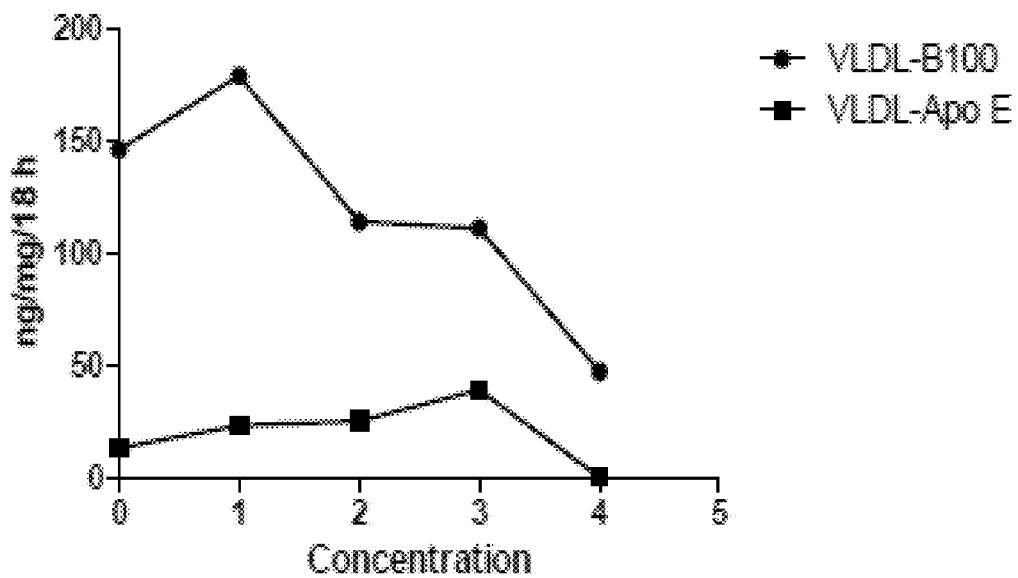
Figure 7C:
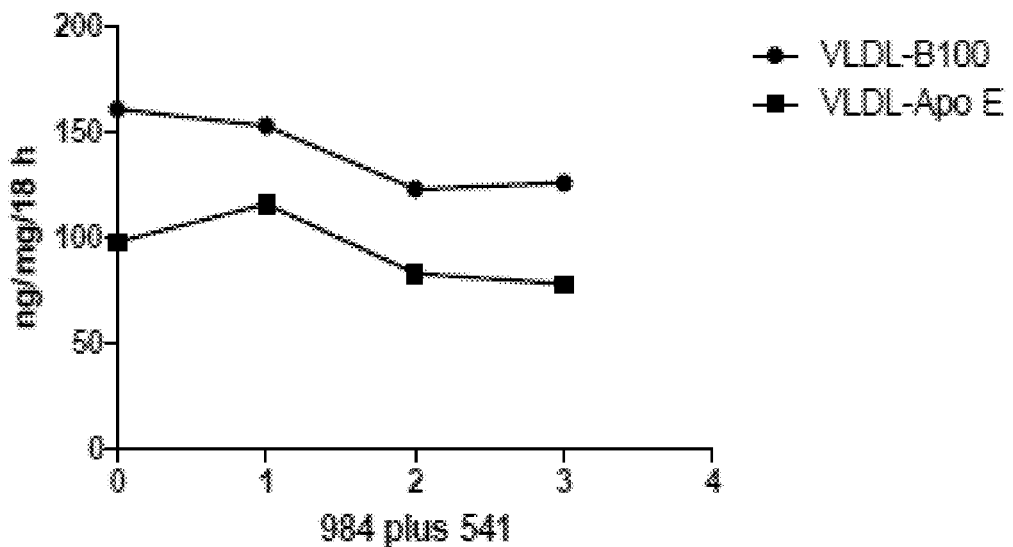

FIGS. 7A-7C show graphs demonstrating an effect of cpd984 and pd541 alone and in combination on the secretion of VLDL-B100 and VLDL-apo E by hepatocytes. McArdle rat hepatocytes were incubated with five media concentrations 0 (no cpd), 1 (0.1 µM), 2 (1 µM), 3 (10 µM) and 4 (25 µM) of cpd984 (FIG. 7A), cpd541 (FIG. 7B), or with a combination of both compounds (FIG. 7C) at indicated concentrations. Hepatocytes were incubated overnight (14-18 h) and media were collected and VLDL-B100 and VLDL-apo E were detected by slot blotting as described above. An anti-rat apoE antibody was used for measurement of VLDL-apo E secretion. Results are the average of triplicate analysis in one study.

An important consideration for VLDL-B100 secretion and the effects of sortilin binding compounds is the possibility of combining compounds binding to SITE 1 and SITE 2. In FIG. 6 it is demonstrated that 984 increases VLDL-B100 secretion in contrast to 541 that decreases VLDL-B100 secretion. These results document different functions of SITE 1 and SITE 2 with influence on VLDL-B100. Apolipoprotein E (apoE) is present on VLDL-B100 particles as well as other apolipoproteins. In FIGS. 7A-7C, 984 and 541 alone and in combination demonstrate effects on secretion of VLDL-B100 and VLDL-apoE by liver cells. As can be seen in FIG. 7A, 984 increases VLDL-B100 and VLDL-apoE in contrast to 541 alone which decreases VLDL-B100 and VLDL-apoE. When given in combination, the effects of 984 are abrogated. The effect of 541 binding to SITE 1 therefore could be used in combination with 984 to alter ligand binding at SITE 2.

Example 4

Figure 8:
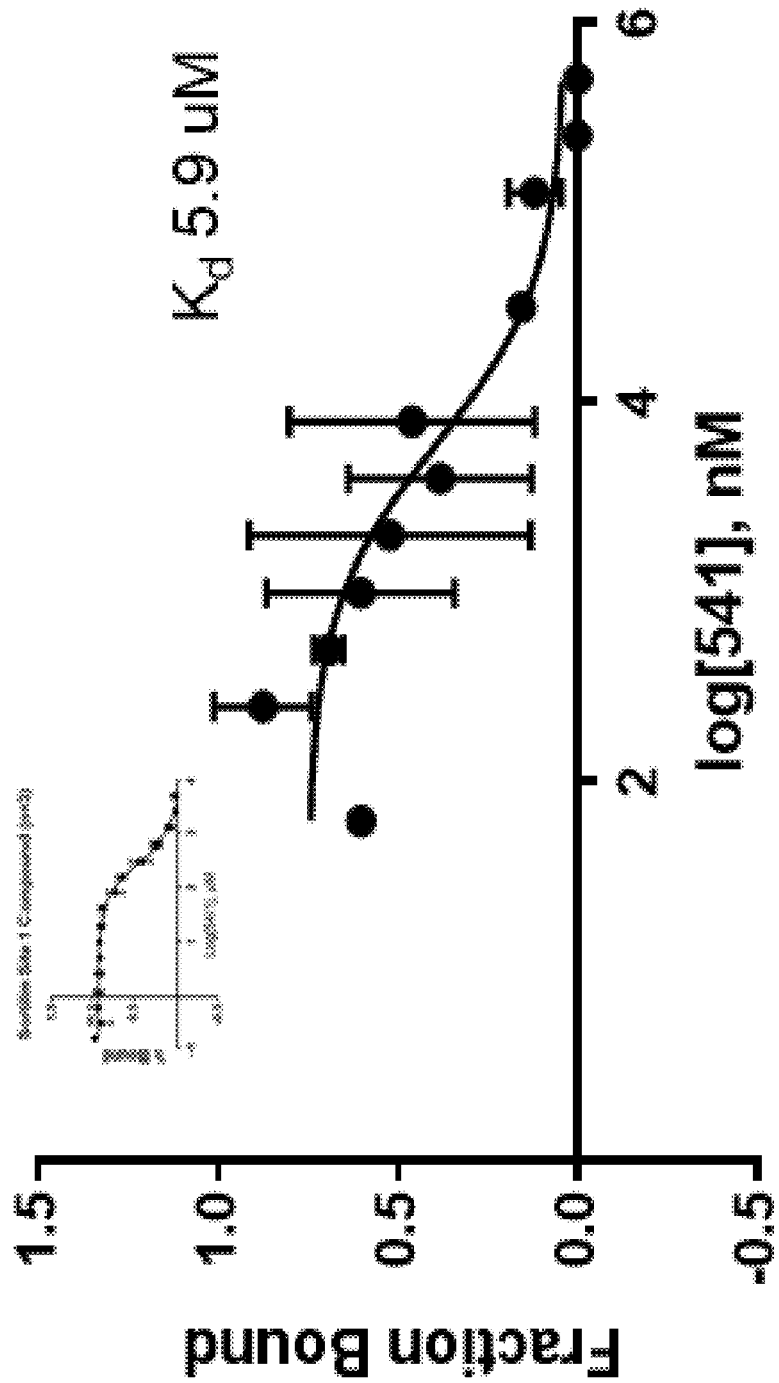
FIG. 8 shows a graph demonstrating the results of two trials of Label Free Thermophoresis of 541 to human sortilin. Due to inherent fluorescence of 541 small molecule, thermophoresis was performed in two different buffer conditions (PBS n=3 and MST n=2) and at two sets of concentration ranges. Because thermophoresis performed in PBS at higher concentration 51 revealed substantial initial fluorescence, results in MST buffer are used for Kd estimation.
Figure 9A:
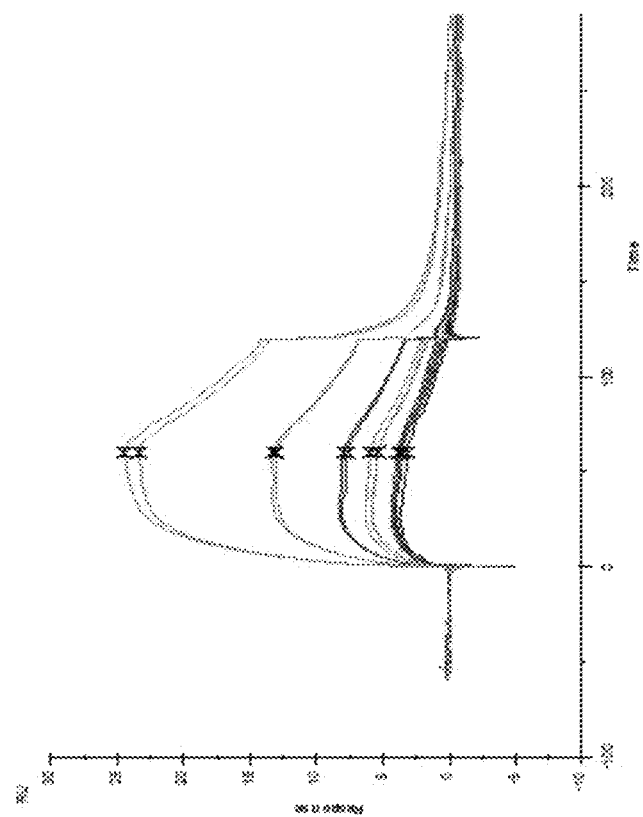
FIGS. 9A-9B show graphs representing the results of two Trials of SPR Indicating Binding of 541 to hsortilin at with Kd of 7.5 μM.
Figure 9B:
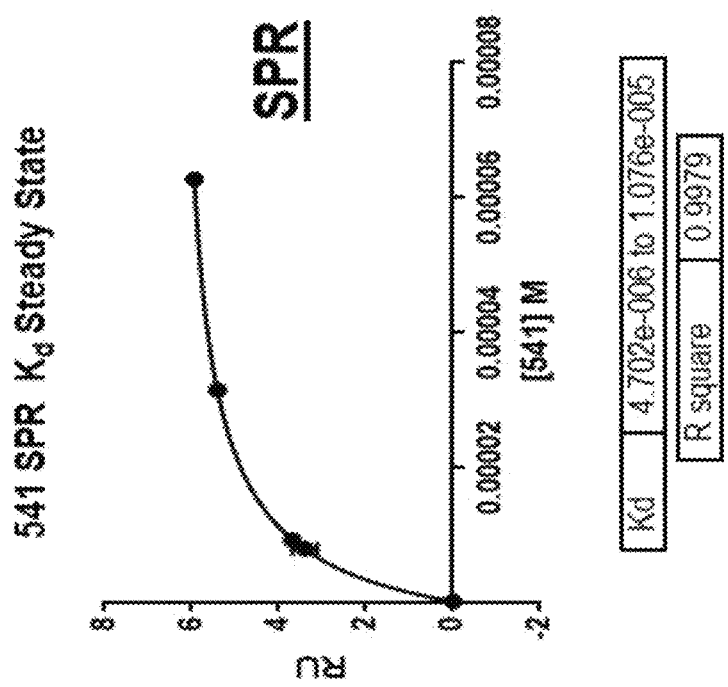
Figures 10A, 10B:
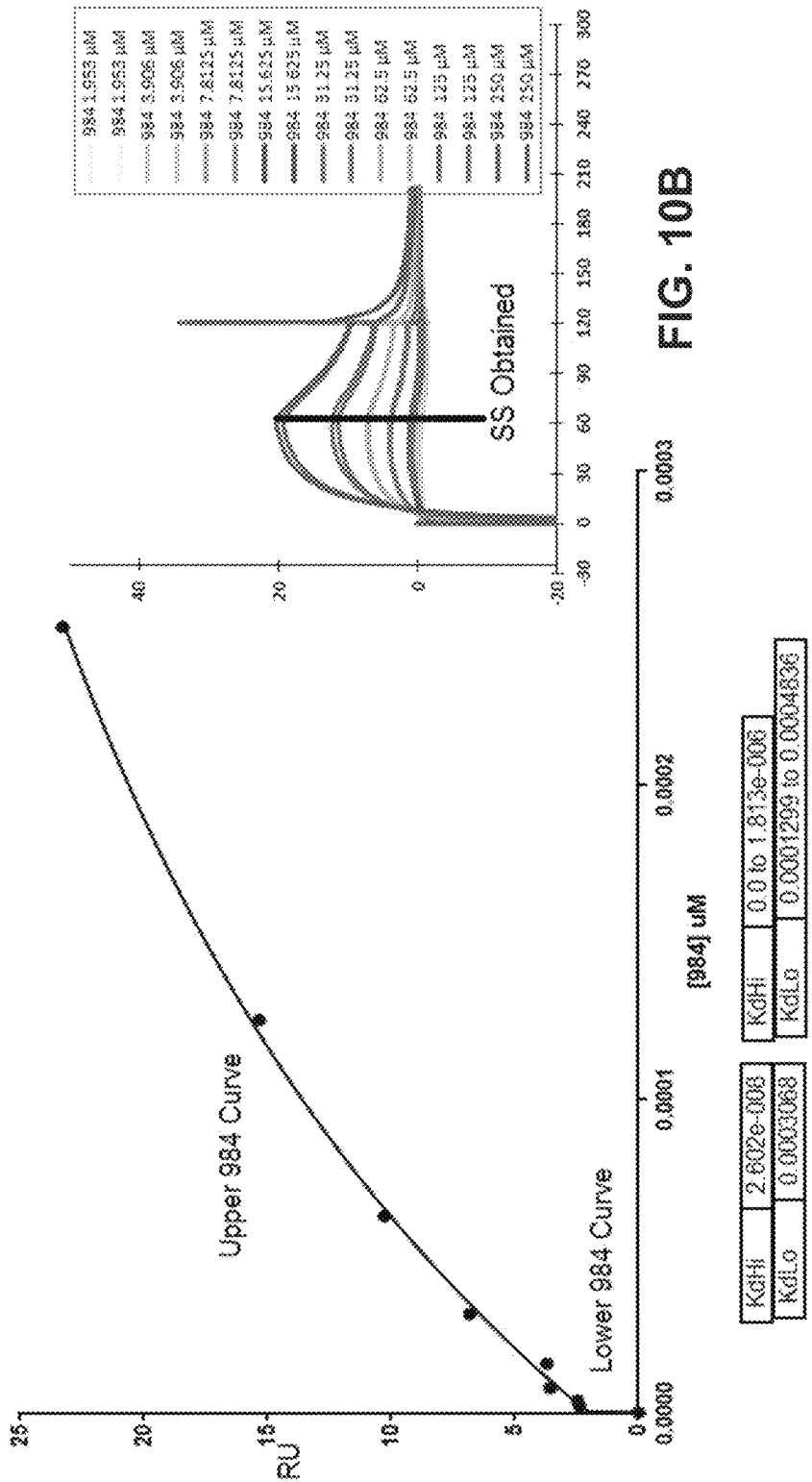
FIGS. 10A-10B show graphs demonstrating the results of SPR of 984 which reveals two different binding ranges. SPR indicates a high and low affinity binding site of cpd984 to human sortilin of hsortilin with Kd of about 200 μM and about 20 nM.
Figure 11A:
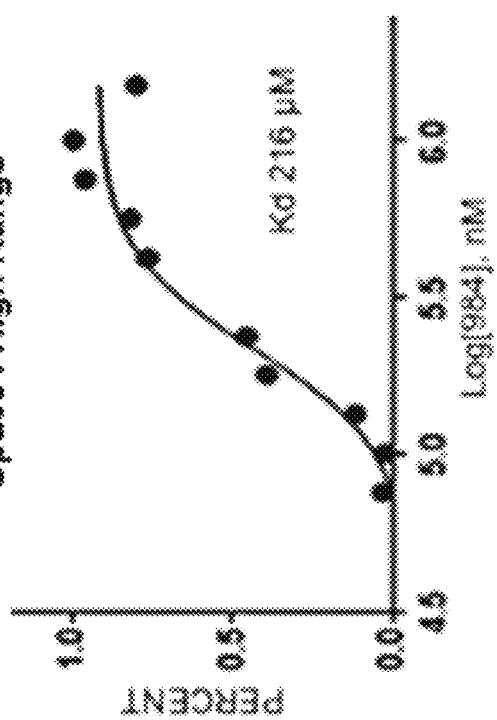
FIGS. 11A-11C show graphs demonstrating the results of thermophoresis of Cpd984, which revealed two different binding ranges with Kd of 7 nM and about 100 to 300 μM.
Figure 11B:
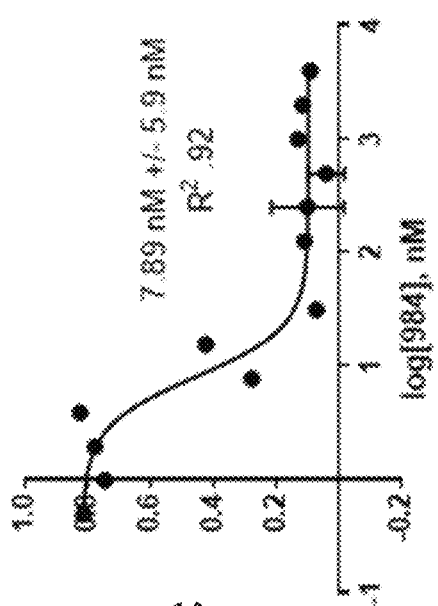
Figure 11C:
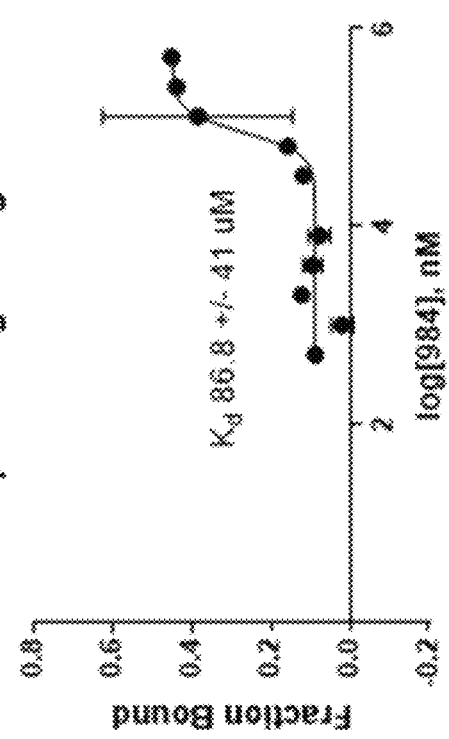

FIG. 8 shows a graph demonstrating the results of two trials of Label Free Thermophoresis of 541 to human sortilin. Due to inherent fluorescence of 541 small molecule, thermophoresis was performed in two different buffer conditions (PBS n=3 and MST n=2) and at two sets of concentration ranges. Because thermophoresis performed in PBS at higher concentration 51 revealed substantial initial fluorescence, results in MST buffer are used for Kd estimation. FIGS. 9A-9B show graphs representing the results of two trials of SPR Indicating Binding of 541 to hsortilin at with Kd of 7.5 µM. FIGS. 10A-10B show graphs demonstrating the results of SPR of 984 which reveals two different binding ranges. SPR indicates a high and low affinity binding site of cpd984 to human sortilin of hsortilin with Kd of about 200 µM and about 20 nM. FIGS. 11A-11C show graphs demonstrating the results of thermophoresis of Cpd984, which revealed two different binding ranges with Kd of 7 nM and about 100 to 300 µM.

FIGS. 8-9B confirm the binding of 541 to human sortilin using surface plasmon resonance (SPR) and thermophoresis. FIGS. 10A-10B confirms binding of 984 to human sortilin using SPR and demonstrates that this binding occurs through low and high affinity binding suggesting two binding sites. FIGS. 11A-11C demonstrate using thermophoresis the binding ranges of 984 for human sortilin including a very high affinity binding site with a Kd of 7 nM which should allow use of 984 at a very low concentration. All of the biologic results for 984 and 541 indicate that the compounds are not restricted with regards to their cellular uptake.

Example 5

The sortilin binding compounds provided herien can be generated using techniques and methods generally known to one of ordinary skill in the art in view of this disclosure. An Examplary synthesis Scheme is shown in Scheme 1.

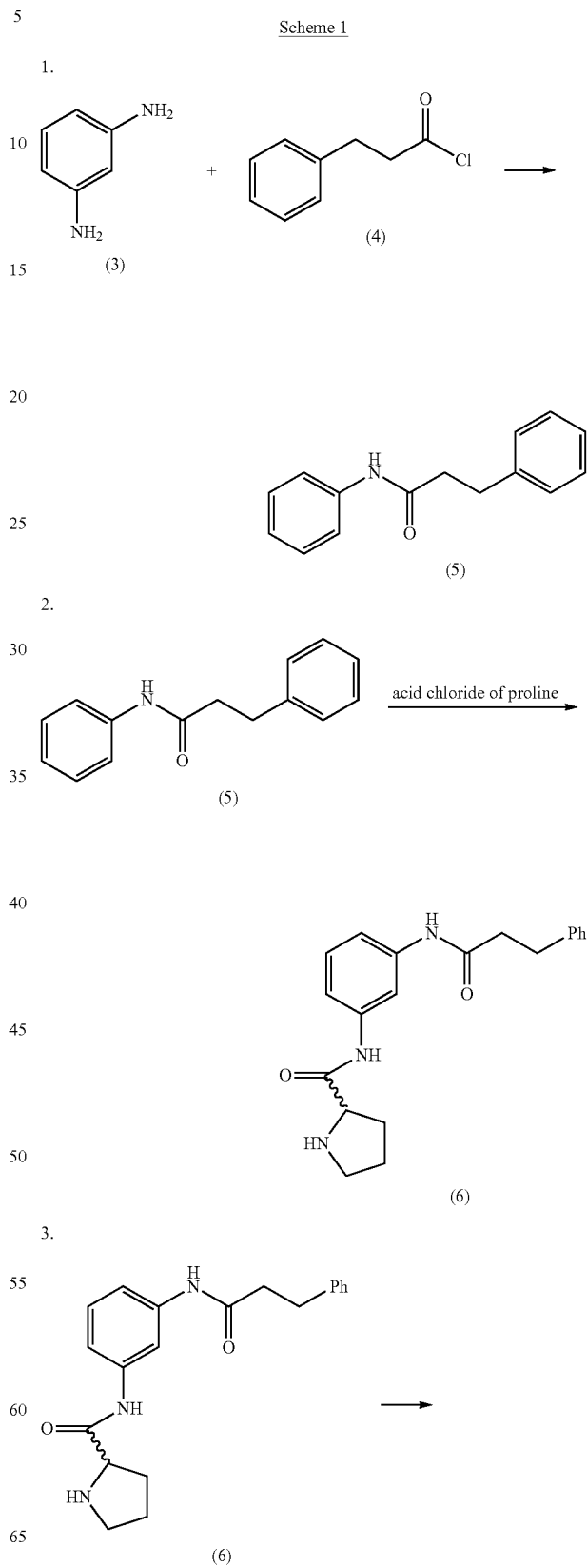

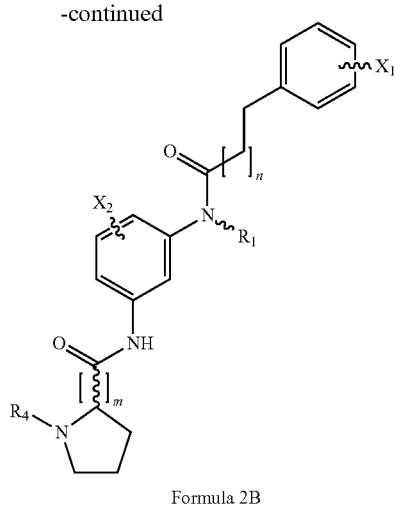
Formula 2B
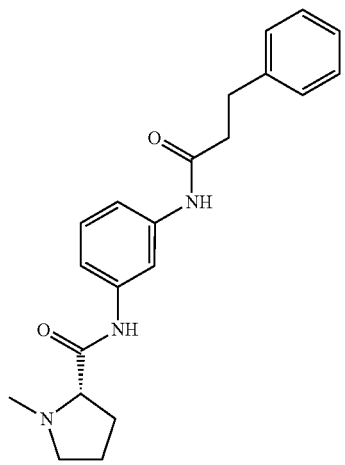
Formula 2A
In some embodiments, the synthesis of sortilin binding compounds can begin with a diamines, analogue, or derivative thereof comb Formula 2A

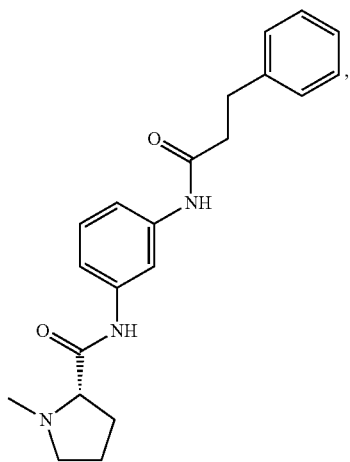

and an effective amount of compound 541 or a pharmaceutical formulation thereof (541)

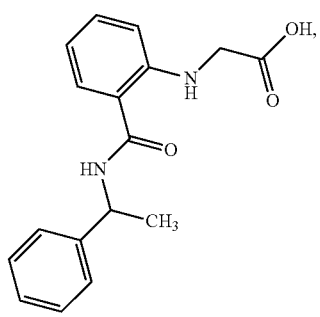

wherein the sortilin ligand is selected from the group consisting of: PCSK9, apolipoprotein B100, phosphatidylinositides, anionic phospholipids, anionic phospholipids contained on VLDL, amyloid beta, amyloid precursor protein, neurotensin or analogues of neurotensin, lipoprotein lipase, apolipoprotein AV and apolipoprotein E.

10. The method of claim 9, wherein the subject suffers from hypercholesteremia or Alzheimer's disease.

11. The method of claim 9, wherein the subject suffers from hepatic steatosis.

12. A pharmaceutical formulation comprising:
an effective amount of a compound having a structure according to Formula 2A Formula 2A

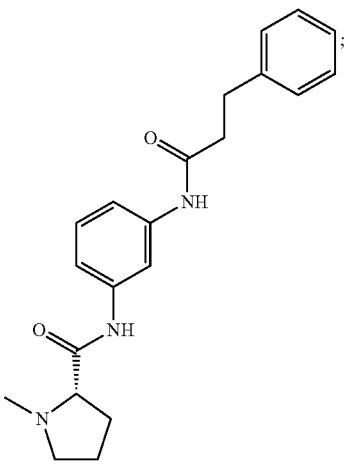

an effective amount of compound 541

(541)

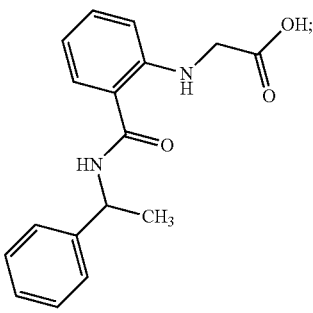

and
a pharmaceutically acceptable carrier.

* * * * *

UNITED STATES PATENT AND TRADEMARK OFFICE
CERTIFICATE OF CORRECTION

PATENT NO. : 10,478,421 B1
APPLICATION NO. : 16/148839
DATED : November 19, 2019
INVENTOR(S) : Robert Pleasants Sparks, Wayne Charles Guida and Janet Lindsay DeHoff-Sparks It is certified that error appears in the above-identified patent and that said Letters Patent is hereby corrected as shown below:

On the Title Page

Item (73), Assignees, please delete:
"University of Florida,"
And replace with:
--University of South Florida--

Signed and Sealed this
Thirtieth Day of June, 2020

Andrei Iancu
*Director of the United States Patent and Trademark Office*